US009605271B2

(12) United States Patent
Takatsuji et al.

(10) Patent No.: US 9,605,271 B2
(45) Date of Patent: Mar. 28, 2017

(54) DISEASE RESISTANT PLANT EXPRESSING WRKY45 UNDER CONTROL OF INFECTION-RESPONSIVE PROMOTER

(71) Applicant: National Institute of Agrobiological Sciences, Ibaraki (JP)

(72) Inventors: Hiroshi Takatsuji, Ibaraki (JP); Shingo Goto, Ibaraki (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 479 days.

(21) Appl. No.: 13/748,334

(22) Filed: Jan. 23, 2013

(65) Prior Publication Data

US 2014/0208458 A1    Jul. 24, 2014

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8239* (2013.01); *C12N 15/8279* (2013.01); *C12N 15/8281* (2013.01); *C12N 15/8282* (2013.01)

(58) Field of Classification Search
None
See application file for complete search history.

(56) References Cited

U.S. PATENT DOCUMENTS

| | | | |
|---|---|---|---|
| 2005/0076406 A1* | 4/2005 | Gebhardt et al. | 800/279 |
| 2007/0016976 A1* | 1/2007 | Katagiri et al. | 800/279 |
| 2010/0122374 A1 | 5/2010 | Takatsuji et al. | |
| 2012/0185969 A1* | 7/2012 | DeBrecht et al. | 800/298 |

FOREIGN PATENT DOCUMENTS

| | | |
|---|---|---|
| EP | 0360750 A2 | 3/1990 |
| EP | 0431829 A1 | 6/1991 |
| JP | H02-186925 A | 7/1990 |
| JP | H03-247220 A | 11/1991 |
| JP | H04-330233 A | 11/1992 |
| JP | H07-250685 A | 10/1995 |
| JP | 2003-088379 A | 3/2003 |
| JP | 2003-199448 A | 7/2003 |
| JP | 2004-329215 A | 11/2004 |
| WO | WO 2006/126671 A1 | 11/2006 |
| WO | WO 2012/121093 A1 | 9/2012 |

OTHER PUBLICATIONS

Chen and Singh, Plant Journal (1999) vol. 19, pp. 667-677.*
Shimono et al, Plant Cell (2007) vol. 19, pp. 2064-2076.*
Mezhir et al, Cancer research (2005) vol. 65 pp. 9479-9484.*
Hu et al, Plant Cell Rep (2011) vol. 30, pp. 539-549.*
Kochetov et al, Gene (2011) vol. 48, pp. 1-6.*
Zhang et al, Plant Journal (2012) vol. 69, pp. 217-226.*
Brown (2006), Chapter 2 of Dissertation, University of California, Davis).*
Shimono et al (Plant Cell (2007) vol. 19, pp. 2064-2076.*
Kochetov et al (Gene (2011) vol. 48, pp. 1-6).*
Zhang et al , Plant Journal (2012) vol. 69, pp. 217-226.*
U.S. Appl. No. 14/004,143, filed Mar. 1, 2012, Inventors Hiroshi Takatsuji et al.
Bahrini, I. et al., "Characterization of a Wheat Transcription Factor, TaWRKY45, and Its Effect on *Fusarium* Head Blight Resistance in Transgenic Wheat Plants," Breeding Science, 2011, pp. 121-129, No. 61.
Bahrini, I. et al., "Overexpression of the Pathogen-Inducible Wheat TaWRKY45 Gene Confers Disease Resistance to Multiple Fungi in Transgenic Wheat Plants," Breeding Science, 2011, pp. 319-326, vol. 61, No. 4; Epub Dec. 15, 2011.
Chen. C. et al., "Potentiation of Developmentally Regulated Plant Defense Response by AtWRKY18, a Pathogen-Induced Arabidopsis Transcription Factor," Plant Physiology, Jun. 2002, pp. 706-716, vol. 129, No. 2.
Chujo, T. et al., "Involvement of the Elicitor-Induced Gene OsWRKY53 in the Expression of Defense-Related Genes in Rice," Biochimica et Biophysica Acta, Jul.-Aug. 2007, pp. 497-505, vol. 1769, No. 7-8; Epub Apr. 22, 2007.
Chujo, T. et al., "Characterization of an Elicitor-Induced Rice WRKY Gene, OsWRKY71," Biosci. Biotechnol. Biochem., Jan. 2008, pp. 240-245, vol. 72, No. 1; Epub Jan. 7, 2008.
Gu, K. et al., "R Gene Expression Induced by a Type-III Effector Triggers Disease Resistance in Rice," Nature, Jun. 23, 2005, pp. 1122-1125, vol. 435, No. 7045.
Ishige, T. President of National Institute of Agrobiological Sciences, Application for Approval of Type 1 Use Regulation of Living Modified Organisms (NIA-OS001-8): Application date: Dec. 22, 2011 (English translation is provided for relevant pages only).
Ishige. T, President of National Institute of Agrobiological Sciences, Application for Approval of Type 1 Use Regulation of Living Modified Organisms (NIA-OS004-2): Application date: Dec. 22, 2011 (English translation is provided for relevant pages only).
Kalde, M. et al., "Members of the *Arabidopsis* WRKY Group III Transcription Factors Are Part of Different Plant Defense Signaling Pathways," Molecular Plant-Microbe Interactions, Apr. 2003, pp. 295-305, vol. 16, No. 4.
Li, J. et al., "The WRKY70 Transcription Factor: A Node of Convergence for Jasmonate-Mediated and Salicylate-Mediated Signals in Plant Defense," The Plant Cell, Feb. 2004, pp. 319-331, vol. 16, No. 2; Epub Jan. 23, 2004.
LiU, X. et al., "OsWRK71, a Rice Transcription Factor, is Involved in Rice Defense Response," Journal of Plant Physiology, Aug. 2007, pp. 969-979, vol. 164, No. 8; Epub Aug. 21, 2006.

(Continued)

*Primary Examiner* — Medina A Ibrahim
(74) *Attorney, Agent, or Firm* — Fenwick & West LLP

(57) ABSTRACT

The present invention relates to plants that have been transformed so as to have both disease resistance and acceptable agronomic traits. More specifically, the present invention relates to transgenic plants that have acquired disease resistance through expression in the plants of a polynucleotide encoding the transcription factor WRKY45 in an infection-responsive manner, and methods for generating the transgenic plants.

21 Claims, 7 Drawing Sheets

(56) References Cited

OTHER PUBLICATIONS

Nagaya, S. et al., "Expression of Randomly integrated Single Complete Copy Transgenes Does Not Vary in *Arabidopsis thaliana*," Plant Cell Physiol., Mar. 2005, pp. 438-444, vol. 46, No. 3; Epub Feb. 2, 2005.

Qiu, Y. et al., "Over-Expression of the Stress-Induced OsWRKY45 Enhances Disease Resistance and Drought Tolerance of Arabidopsis," Environmental and Experimental Botany, 2009, pp. 35-47, vol. 65, No. 1.

Qiu, D. et al., "OsWRKY13 Mediates Rice Disease Resistance by Regulating Defense-Related Genes in Salicylate- and Jasmonate-Depdendent Signaling," Molecular Plant-Microbe Interactions, May 2007, pp. 492-499, vol. 20, No. 5.

Qiu, Y. et al., "Cloning and Analysis of Expression Profile of 13 WRKY Genes in Rice," Chinese Science Bulletin, Oct. 2004, pp. 2159-2168, vol. 49, No. 20.

Robatzek, S. et al., "Targets of *At*WRKY6 Regulation During Plant Senescence and Pathogen Defense," Genes & Development, May 1, 2002, pp. 1139-1149, vol. 16, No. 9.

Satoh, J. et al., "The 5'-Untranslated Region of the Tobacco *Alcohol Dehydrogenase* Gene Functions as an Effective Translational Enhancer in Plant," Journal of Bioscience Bioengineering, 2004, pp. 1-8, vol. 98, No. 1.

Shimono, M. et al., "Rice WRKY45 Plays a Crucial Role in Benzothiadiazole-Inducible Blast Resistance," The Plant Cell, Jun. 2007, pp. 2064-2076, vol. 19, No. 6 Epub Jun. 29, 2007.

Sugio, T. et al., "The 5'-Untranslated Region of the *Oryza sativa* Alcohol Dehydrogenase Gene Functions as a Translational Enhancer in Monocotyledonous Plant Cells," Journal of Bioscience Bioengineering, Mar. 2008, pp. 300-302, vol. 105, No. 3.

Tao, Z. et al., "A Pair of Allelic WRKY Genes Play Opposite Roles in Rice-Bacteria Interactions," Plant Physiology, Oct. 2009, pp. 936-948, vol. 151, No. 2; Epub Aug. 21, 2009.

Tian, D. et al., "Constitutive Heterologous Expression of *avrXa27* in Rice Containing the *R* Gene *Xa27* Confers Enhanced Resistance to Compatible *Xanthomonas oryzae* Strains," Molecular Plant Pathology, Jan. 2009, pp. 29-39, vol. 10, No. 1.

Windhovel, U. et al., "Expression of *Erwinia uredovora* Phytoene Desaturase in *Synechococcus* PCC7942 Leading to Resistance Against a Bleaching Herbicide," Plant Physiol., Jan. 1994, pp. 119-125, vol. 104, No. 1.

Xie. et al., "Annotations and Functional Analyses of the Rice *WRKY* Gene Superfamily Reveal Positive and Negative Regulators of Abscisic Acid Signaling in Aleurone Cells," Plant Physiology, Jan. 2005, pp. 176-189, vol. 137, No. 1; Epub Dec. 23, 2004.

Yu, D. et al., "Evidence for an Important Role of WRKY DNA Binding Proteins in the Regulation of *NPR1* Gene Expression," The Plant Cell, Jul. 2001, pp. 1527-1540, vol. 13, No. 7.

\* cited by examiner

SEQUENCE LISTING

<160> NUMBER OF SEQ ID NOS: 12

<210> SEQ ID NO 1
<211> LENGTH: 1453
<212> TYPE: DNA
<213> ORGANISM: Oryza sativa

<400> SEQUENCE: 1

```
gggtgctttg agctccatca ccagctgagc tgcgaggaag agagagtgcg agagtgcgcg      60
gcagcggcag tgtagtgtca gtcactgggt gtgcgcttgc ttgcttggat tgaggatgac     120
gtcatcgatg tcgccggcgc cggcgccggc gtacgcgcag gtgatggagg acatggagaa     180
```

```
gggaaggag    ctggcggcgc    agctgcaggg    gctcctccgc    gactcgccgg    aggccggccg        240
cttcgtcgac    cagattctcc    acaccttctc    ccgggcgatg    cgggcgctcg    acaaggcggc        300
ggtctccgcc    gccggaggag    aagggtcgga    ggtgcagagc    gaggtcacct    gcggggggcgg       360 ggccagcgcc    ggcgggaaga    ggaaagcccc    cgccgccgac    cggaaggcca    actgccgcag        420
gaggacgcag    caatcgtccg    ggaattcggt    ggtcgtcaag    aacctcgacg    acggccaggc        480
atggcgcaag    tacgggcaga    aggagatcca    aaactccaag    cacccaaagg    cctacttccg        540
gtgcacgcac    aagtacgacc    agctgtgcac    ggcgcagcgg    caggtgcagc    gctgcgacga        600
cgacccggcg    agctacaggg    tcacctacat    cggcgagcac    acctgccggg    acccggccac        660
cgcccccatc    atcgcggcgc    acgtcatcca    ccaggtcgcc    gccggcgaca    cgacgacgg         720 ctgcggcggc    ctccaagcgg    ggtcccgcct    catcagcttc    gtcgccgcgc    cggcggcgcc        780
agtagacgct    gccgcggcgc    cgacgaccag    cacgatcacc    acggtcaccg    cgccgggccc        840
gctgctgcag    ccgctcaagg    tggagggcgg    cgtcggctcg    tccgaccagg    aggaggtgct        900
gagcagcctc    acgcccggca    gctccgcggc    gcgcggcggc    ggcggcggcg    gcggagtcgc        960
gggtcccttc    gggccggacc    agggcgatgt    cacgtcctcc    ctgcactgga    gctacgacgg       1020
cgtcgccggc    atggagttct    tcaagaacga    cgaggttgtc    ttcgatctgg    acgacattat       1080
gggtttgagc    ttttgatcac    cgaagaatca    tggatggaca    cgggccgggt    aaaacgatcg       1140
aaagaagatg    gattccacgc    gtgtgtacag    aaataattag    cggcagcgcg    gatcttaatt       1200
tggaacttgc    aaagatactc    ctaattagcc    tggctagatt    agtttgtaaa    ttccttgttg       1260
atgtgtcgtc    tcagctttaa    gctgcagaca    tgctagcaag    taacaacacg    attagtacgt       1320
agtaatgtgg    ttcttgatta    tgagctgggg    gtcttaacct    tttttgtgtg    acaagcaaga       1380
gaagaggatt    tgggtacaat    gtaatcctgt    tcttccgctt    tcgaaaaaaa    aaaacatata       1440
gcttcacgtg    cct                                                                     1453
```

<210> SEQ ID NO 2
<211> LENGTH: 326
<212> TYPE: PRT
<213> ORGANISM: Oryza sativa

<400> SEQUENCE: 2

```
Met Thr Ser Ser Met Ser Pro Ala Pro Ala Pro Ala Tyr Ala Gln Val
1               5                   10                  15

Met Glu Asp Met Glu Lys Gly Lys Glu Leu Ala Ala Gln Leu Gln Gly
            20                  25                  30

Leu Leu Arg Asp Ser Pro Glu Ala Gly Arg Phe Val Asp Gln Ile Leu
        35                  40                  45

His Thr Phe Ser Arg Ala Met Arg Ala Leu Asp Lys Ala Ala Val Ser
    50                  55                  60

Ala Ala Gly Gly Glu Gly Ser Glu Val Gln Ser Glu Val Thr Cys Gly
65                  70                  75                  80

Gly Gly Ala Ser Ala Gly Gly Lys Arg Lys Ala Pro Ala Ala Asp Arg
                85                  90                  95

Lys Ala Asn Cys Arg Arg Arg Thr Gln Gln Ser Ser Gly Asn Ser Val
            100                 105                 110

Val Val Lys Asn Leu Asp Asp Gly Gln Ala Trp Arg Lys Tyr Gly Gln
        115                 120                 125

Lys Glu Ile Gln Asn Ser Lys His Pro Lys Ala Tyr Phe Arg Cys Thr
    130                 135                 140
```

His Lys Tyr Asp Gln Leu Cys Thr Ala Gln Arg Gln Val Gln Arg Cys
145                 150                 155                 160

Asp Asp Asp Pro Ala Ser Tyr Arg Val Thr Tyr Ile Gly Glu His Thr
            165                 170                 175

Cys Arg Asp Pro Ala Thr Ala Pro Ile Ile Ala Ala His Val Ile His
            180                 185                 190

Gln Val Ala Ala Gly Asp Asn Asp Asp Gly Cys Gly Gly Leu Gln Ala
        195                 200                 205

Gly Ser Arg Leu Ile Ser Phe Val Ala Ala Pro Ala Pro Val Asp
    210                 215                 220

Ala Ala Ala Ala Pro Thr Thr Ser Thr Ile Thr Thr Val Thr Ala Pro
225                 230                 235                 240

Gly Pro Leu Leu Gln Pro Leu Lys Val Glu Gly Val Gly Ser Ser
            245                 250                 255

Asp Gln Glu Glu Val Leu Ser Ser Leu Thr Pro Gly Ser Ser Ala Ala
            260                 265                 270

Arg Gly Gly Gly Gly Gly Gly Val Ala Gly Pro Phe Gly Pro Asp
        275                 280                 285

Gln Gly Asp Val Thr Ser Ser Leu His Trp Ser Tyr Asp Ala Val Ala
        290                 295                 300

Gly Met Glu Phe Phe Lys Asn Asp Glu Val Val Phe Asp Leu Asp Asp
305                 310                 315                 320

Ile Met Gly Leu Ser Phe
            325

<210> SEQ ID NO 3
<211> LENGTH: 1999
<212> TYPE: DNA
<213> ORGANISM: Oryza sativa

<400> SEQUENCE: 3

```
atccattgcc gatccatcta catgacatga aaaaaaatcg tacacaaata attattctta      60
caataatgac agtcatacaa taattataag ataattacaa actcttcaa cagtcataca     120
ataataacat atctttattc atacaaaaat cataaaatat tacaccaaat aattcttatt    180
tactatttct aaagttttaa actaatatta atgtgtttta cttcttttaa ttttcatttt    240
agtttgtttt ctgttattga agattaactt tcactatatt ttccttctca aatattttat    300
aaaaccttct ttagcaaatc aactaaattt atatatattc tttcttctcc acacaaattt    360
tctctctcat cacaactaaa ttttggagac aaaaagtgt gcaaaacata gctccaaatg     420
taatatgaca aaaaaaacat tggaggataa agttgcaaac cttttaggca cctccgattt    480
gtatgtaatc accaaaataa attcactaga aattttggca tgacctcccc tcttttttga    540
agaaattttg aagcttgctt gggcagctgg aggagaaaga agacatatat ataggggt     600
gggactttag tcccggttgg tgttaccaac caggactaaa gatcacgggg gggggggg      660
ggggcgaca ggccctagta gcatttgaac caggactaaa gattaaatat gtcaaacatg     720
gtcaaacatg ttataccatg ttgatcatgc atgtagctaa gtgcgattta tatcttatac    780
atttgcataa aattttgaa taagacgaat ggttaaacat atgagaaaaa gtcaacggcg     840
ttttctatta aaaacggag gtagtattac ttagtattca tgcatgtatg catggacatg     900
cagccttcga gtgcacagcg agttttgta tagtgaaaaa aaatgatga gatggaagga     960
aaggatggca tacgttcggt ggggagggga attcggaggt ttatttttt tttggtaag   1020
tacacgcgcg cacgtacata ctactgaagg agaagaggtg gggccctggt gtcttgttag   1080
```

```
ttttaaggtt aatctaatct aacggtttat aatattggat tcaccaactt aaatgaaaac    1140
gaagggacac atgttttgct ttttttctcag aattttttga atttctctaa tttattagaa    1200
cgccacatga cggcttgaga gtgtttgtag gaagtttaat ggacgtttag tatataataa    1260
tagatagaat ttcttggatt tctctaattt attagagcgc cacatgacgg cttgagagcg    1320
tttgtatgaa gtttaatgta cttttagtat ataatagata gatagataga tagatagaag    1380 atagttttg tatgagttgt tcgatgtttt acgctcccaa atatattaat acattggatc    1440 accatttaa atttattata gataagttta atacgaaaat ttcagatttg ttttcttaat    1500
ttttatgaac aacatttgca tacaacatct ggtcgtaata actacgttga atattaccct    1560
cttgatgact tgactaattt tagacaaaag atggtcaccc acccagcttt tcattgaaag    1620
tataagagtt catacagtgc aaaaaggaac aaaggtaaaa taaaaggaaa gtaaaaatcc    1680
caagtcctgc gtacaaatct atagttcaag acatacacat cgccttccaa ccgaggtcga    1740
gttgccccgg tgccatgtct tattcgtgga attctatgtc caagtgcata ctttgcgggg    1800
gtaaaatttt ctacacgtat gttgccaaaa tttctgctaa gttttcgtg gccaactcga    1860 gaaaattctt acacagccag tctataaata ctcacacatt tcacaaaaaa atacttgcaa    1920
catcaaagct acacaggtag aatcatcgac cgtaagtaag tactactcct acgtacatta    1980
agtgtgagct tgattaact                                                 1999
```

<210> SEQ ID NO 4
<211> LENGTH: 1951
<212> TYPE: DNA
<213> ORGANISM: Oryza sativa

<400> SEQUENCE: 4

```
ccagcagata ttggattgct gattcttacg aagagagatt cagttctggt cttgagcctg     60
aaaatgttga caaggtagac tgctcctgaa actatacatg tggcagcgtt atgccttaaa    120
cttattatgc ttttaattta caatggaatt gctgaagatg tgattttatt ttcaccagga    180
gttcttaaga ctctggttca agaacaattg caatccatac gaagatgcgg tataccattt    240
ttccttaaac cacttaagca ttttccatag taagcaaatg ttgataatta gtgaaatatg    300
agatgtccat gaataggtcc acgtataaat tccatgtcca ttgactgcat gtttgtttgt    360
cttttgaagg ctctttgttt ttgtgaaaac tcatttcatg tttatctgtt actttaaaat    420
actcaggttc tgcctgaagc tccagaagaa ctagtttgtg aactagcttg gcggtatgtc    480
tatttctctg agtttgttct agtacttctc atttcagagc atgttcaacc aacaacttta    540
tgtgcttctc tatgtacatg aatctcgtac aaacatgata tcatattggt tgaattatag    600
tttgcttaaa tatccaccac aggtacattt tcctgtttga dacaattaca aacacaaagt    660
tcgagatccc caaaactcag gtatgtgacg acagtttggt gaatttgctg taactgacaa    720
ccatatactt aaaacatttt tgttaaatgc aggagccgat tcacgaaaga atatcaagga    780
atgttgcaca agccttgcag aacctttgat tgtggataag gaagaggatt tccagaacaa    840
aaacttgctt gctgatgaga ataagaggtg cacttctgga cttctggtac cggcattact    900
aataataata tcagcgtacg ttcatgccgt ctatcattca aagtatacgt gtgctccgag    960
atgtaatatg gttggaaaca actatagcca gaatcgcctg gcaatactct ctgccctaa    1020 tagtttccct gttgtgaggg tcagtgagtg atagagcgcc atacacggta tgcatgattg    1080
cgtgctaata ttttttttcac cctgtgatgt aacatttctt gggggttcaca tcgtttatca    1140
```

```
tgatgacact accattatac tccctccgtt ctaaaatata atcattttta gctatgaatc      1200
tagcatgtcc agattcatag ctaaaaatac ttacattttg ggacggaggg agtagatatt      1260
attaacgtgt gggataatag gagggatggt gagacctgca tactagtgac cataatgata      1320
atgatattat attatactcc ctccgttcta aaatataagc attttttagct atgaatctag     1380 catgtccaga ttcatagcta aaaatactta cattttggga cggagggagt agatattaac     1440
gtgtgggata ataggaggga tggtgagacc cgcatactag tgaccataat gataatgata     1500
ttatggtaat gataatgaca ttatggtaga gtattctcac cccatttttct gtgtaacaaa     1560 caaataatat cgaagaggct gagttcaagt ttgctccgcc tctagtgaaa gtgtgatcct      1620
atacttcaga acacttcagt ttagaaacaa acaatttcta atgatgccaa gtcgtttgtt     1680
attactagca ccgggcaata ttttctccat tttgtcaaac tcccacaaaa tccgtacaga    1740
tggaccattc attttagaaa gtctctcttg tcagtgtcac tgatcgatat atcgatagag    1800
gaaagggaag aagaatcagc cgcttaaaat gtagagtact cccaagcaac gttgacttga   1860
cttcccaact cccaactccc aacttcccaa gcctttttaa tcccaaagag gggatcagca   1920
gctgcaagtg catcagcagc gagttccagc c                                    1951

<210> SEQ ID NO 5
<211> LENGTH: 101
<212> TYPE: DNA
<213> ORGANISM: Oryza sativa

<400> SEQUENCE: 5
gaattccaag caacgaactg cgagtgattc aagaaaaaag aaaacctgag ctttcgatct       60
ctacggagtg gtttcttgtt ctttgaaaaa gagggggatt a                         101

<210> SEQ ID NO 6
<211> LENGTH: 498
<212> TYPE: DNA
<213> ORGANISM: Artificial Sequence
<220> FEATURE:
<223> OTHER INFORMATION: An artificially synthesized nucleotide sequence

<400> SEQUENCE: 6
ggatccgctg aaatcaccag tctctctcta caaatctatc tctctctata ataatgtgtg        60
agtagttccc agataaggga attagggttc ttatagggtt tcgctcatgt gttgagcata      120
taagaaaccc ttagtatgta tttgtatttg taaaatactt ctatcaataa aatttctaat      180
tcctaaaacc aaaatccagt gatccgcggc cgcgagctcg aatttccccg atcgttcaaa      240
catttggcaa taaagtttct taagattgaa tcctgttgcc ggtcttgcga tgattatcat      300
ataatttctg ttgaattacg ttaagcatgt aataattaac atgtaatgca tgacgttatt      360
tatgagatgg gtttttatga ttagagtccc gcaattatac atttaatacg cgatagaaaa      420
caaaatatag cgcgcaaact aggataaatt atcgcgcgcg gtgtcatcta tgttactaga      480
tcgggaattc ttaattaa                                                   498

<210> SEQ ID NO 7
<211> LENGTH: 13
<212> TYPE: DNA
<213> ORGANISM: Artificial Sequence
<220> FEATURE:
<223> OTHER INFORMATION: An artificially synthesized nucleotide sequence

<400> SEQUENCE: 7
agcttggcca aat                                                         13
```

```
<210> SEQ ID NO 8
<211> LENGTH: 6
<212> TYPE: DNA
<213> ORGANISM: Artificial Sequence
<220> FEATURE:
<223> OTHER INFORMATION: An artificially synthesized nucleotide sequence

<400> SEQUENCE: 8 tggcca                                                                     6

<210> SEQ ID NO 9
<211> LENGTH: 21
<212> TYPE: DNA
<213> ORGANISM: Artificial Sequence
<220> FEATURE:
<223> OTHER INFORMATION: An artificially synthesized nucleotide sequence

<400> SEQUENCE: 9
agctggcgcg ccatttaaat a                                                   21

<210> SEQ ID NO 10
<211> LENGTH: 21
<212> TYPE: DNA
<213> ORGANISM: Artificial Sequence
<220> FEATURE:
<223> OTHER INFORMATION: An artificially synthesized nucleotide sequence

<400> SEQUENCE: 10
agcttattta aatggcgcgc c                                                   21

<210> SEQ ID NO 11
<211> LENGTH: 24
<212> TYPE: DNA
<213> ORGANISM: Artificial Sequence
<220> FEATURE:
<223> OTHER INFORMATION: An artificially synthesized nucleotide sequence

<400> SEQUENCE: 11
tgtgtgacaa gcaagagaag agga                                                24

<210> SEQ ID NO 12
<211> LENGTH: 20
<212> TYPE: DNA
<213> ORGANISM: Artificial Sequence
<220> FEATURE:
<223> OTHER INFORMATION: An artificially synthesized nucleotide sequence

<400> SEQUENCE: 12
aacgatcggg gaaattcgag                                                     20
```

DISEASE RESISTANT PLANT EXPRESSING WRKY45 UNDER CONTROL OF INFECTION-RESPONSIVE PROMOTER

REFERENCE TO A SEQUENCE LISTING

This application includes a Sequence Listing submitted electronically as a text file named 22551_US_Sequence_Listing.txt, created on Jan. 23, 2013, with a size of 13 KB and comprising 12 sequences. The sequence listing is hereby incorporated by reference.

FIELD OF THE INVENTION

The present invention relates to plants having disease resistance. In particular, the present invention relates to plants that have been transformed to have both disease resistance and acceptable agronomic traits. More specifically, the present invention relates to transgenic plants that have acquired disease resistance through expression in the plants of a polynucleotide encoding the transcription factor WRKY45 in an infection-responsive manner, and methods for generating the transgenic plants.

BACKGROUND

In crop production, there is a steady demand for stable production of high-quality plants and reduction of pesticide dependency. To that end, researchers are actively improving, breeding, and developing cultivars of plants resistant to pests and pathogenic microbes through useful plant biotechnologies, such as plant cell fusion and recombinant DNA techniques. Transformed plants resistant to herbicides (Japanese Patent Application Kokai Publication No. (JP-A) H02-186925 (unexamined, published Japanese patent application)), viruses (JP-A (Kokai) H04-330233), and pests (JP-A (Kokai) H03-247220) have already been produced using recombinant DNA techniques. Furthermore, several types of transformed plants resistant to plant pathogenic microbes have been produced, for example, transformed plants showing resistance to a pathogenic filamentous fungus, which are produced by introducing a gene of an enzyme that inactivates a toxin produced by the pathogenic fungus (Windhovel, U. et al., Plant Physiol., 104, 119-125 (1994)); transformed plants showing resistance to at least one pathogenic bacterium, which are produced by introducing a gene of an insect-derived antibacterial protein (JP-A (Kokai) H07-250685); transformed plants resistant to complex disease, which are produced by introducing a Japanese mustard spinach-derived gene (JP-A (Kokai) 2004-329215); transformed plants resistant to multiple diseases, which are produced using the thionine gene (JP-A (Kokai) 2003-88379); and transformed plants resistant to complex diseases, which are produced using an acidic thaumatin-like protein gene (JP-A (Kokai) 2003-199448). However, the introduction of these defense genes into plants did not confer sufficiently strong resistance to multiple pathogens. Furthermore, some of the introduced genes have harmful effects on the growth, fertility, and such of the transformants, thereby hindering their practical application.

WRKY transcription factors have been reported to be involved in disease resistance of dicots such as Arabidopsis (Kalde, M. et al., Mol. Plant Microbe Interact., 16, 295-305 (2003); Li, J. et al., Plant Cell, 16, 319-331 (2004); Robatzek, S. et al., Genes Dev., 16, 1139-1149 (2002); Yu, D. et al., Plant Cell, 13, 1527-1540 (2001); Chen, C. et al., Plant Physiol., 129, 706-716 (2002)). Several OsWRKY genes that confer disease resistance in rice plants have been reported in recent years (Xie, Z. et al., Plant Physiol., 137, 176-189 (2005); Qiu, Y. et al., Chinese Science Bulletin, 49(20), 2159-2168 (2004); Qiu, D. et al., Mol Plant Microbe Interact, 20(5), 492-499 (2007); Liu, X. et al., J Plant Physiol, 164(8), 969-979 (2007); Chujo, T. et al., Biochimica et Biophysica Acta (BBA)—Gene Structure and Expression, 1769(7-8), 497-505 (2007); Chujo, T. et al., Biosci Biotechnol Biochem, 72(1), 240-245 (2008); Tao, Z. et al., Plant Phys., 151, 936-948 (2009); Qiu, Y. and D. Yu, Environmental and Experimental Botany, 65(1), 35-47 (2009)). The transcription factor WRKY45 of rice (OsWRKY45) is known to confer a significantly strong resistance to rice blast, bacterial leaf blight, and the like (a complex disease resistance). WRKY45 has also been reported in wheat (TaWRKY45) (Bahrini et al., Breeding Science 61: 121-129 (2011); Bahrini et al., Breeding Science 61: 319-326 (2011)). When OsWRKY45 is expressed using the maize ubiquitin (Zmubi) promoter ($P_{ZmUbi}$) which is a strong constitutive promoter, the rice shows a strong complex disease resistance to rice blast, bacterial leaf blight, and brown spot (WO 2006/126671). However, in the WRKY45-expressing rice, growth delay and decrease in the rice grain yield are observed (Shimono, M. et al., Plant Cell, 19, 2064-2076 (2007)), suggesting that overexpression of the WRKY45 gene may have resulted in problems of deterioration of rice growth and yield.

Cis elements that are known to influence modulation of gene expression include transcriptional promoters, transcriptional/translational enhancers, transcriptional terminators, and such. In an attempt to balance complex disease resistance and agronomic traits, techniques of expressing WRKY45 using the OsUbil, EF1a, and OsUbi7 promoters which have a weaker constitutive activity (WO 2012/121093) have been developed. Besides these promoters, many promoters are known as transcriptional promoters, and examples include the promoter of glutathione-S-transferase (GST) gene and the promoter of one of the PR protein genes (PR1b promoter). The PR1b promoter is a promoter induced upon infection by a pathogenic microorganism, and there have been reports that driving the expression of Xanthomonas oryzae pv. oryzae (Xoo)-resistance gene by this promoter resulted in resistance against Xoo (Gu et al., Nature, Vol 435, 23 Jun. 2005, 1122-1125 (2005); Tian and Yin, Molecular Plant Pathology, Vol 10(1), 29-39 (2009)). As an example of the translational enhancers, the 5'-UTR of the rice alcohol dehydrogenase (OsADH) gene is known (Sugio T et al., Journal of Bioscience and Bioengineering, Vol. 105, No. 3, 300-302 (2008)). Further, it has been reported that the UTRs of the tobacco and Arabidopsis ADH genes can be used as translational enhancers (Satoh, J. et al., Journal of bioscience and bioengineering, 98, 1-8 (2004); Nagaya, S. et al, Plant Cell Physiol., 46 (3), 438-444 (2005)). Examples of transcriptional terminators include the 35S terminator (35ST) of the Cauliflower mosaic virus (CaMV) and the terminator of Nopaline synthase (Nos) gene.

SUMMARY

The inventors discovered that the balance between complex disease resistance and agronomic traits could be further improved by expressing the transcription factor WRKY45 which is a plant-derived protein in an infection-responsive manner.

In one aspect, the present invention provides a transgenic plant having both complex disease resistance and acceptable agronomic traits through expression in an infection-responsive manner of a plant-derived protein having a function of improving plant disease resistance, specifically, a polynucleotide encoding the transcription factor WRKY45.

In some embodiments of the invention, the plant comprises a functional WRKY45 gene and the WRKY45 gene is operably linked to an infection-responsive promoter and a translational enhancer. Moreover, in one embodiment, the plant is a monocot plant, preferably rice.

In some embodiments of the plant, the WRKY45 gene is the rice OsWRKY45 gene, and in one embodiment the gene has the amino acid sequence of SEQ ID NO: 2. In another embodiment, the WRKY45 gene has a sequence at least 95% identical to the amino acid sequence of SEQ ID NO: 2.

In some embodiments of the plant, the infection-responsive promoter is the PR1b promoter, and in one embodiment, the promoter has the nucleotide sequence of SEQ ID NO: 3. In another embodiment, the PR1b promoter has a sequence at least 95% identical to the nucleotide sequence of SEQ ID NO: 3.

In some embodiments of the plant, the infection-responsive promoter is the GST promoter, and in one embodiment, the promoter has the nucleotide sequence of SEQ ID NO: 4. In another embodiment, the GST promoter has a sequence at least 95% identical to the nucleotide sequence of SEQ ID NO: 4.

In some embodiments of the plant, the translational enhancer is the 5'-unstranslated region of the alcohol dehydrogenase gene (ADH-UTR), and in one embodiment, the enhancer has the nucleotide sequence of SEQ ID NO: 5. In another embodiment, the translational enhancer has a sequence at least 95% identical to the nucleotide sequence of SEQ ID NO: 5.

In some embodiments of the plant, the WRKY45 gene is operably linked to a tandem terminator comprising two terminator sequences linked in tandem. In one embodiment, the tandem terminator comprises the Nos terminator and the Cauliflower mosaic virus 35S terminator, and in one embodiment, the tandem terminator has the nucleotide sequence of SEQ ID NO: 6. In another embodiment, the tandem terminator has a sequence at least 95% identical to the nucleotide sequence of SEQ ID NO: 6.

In some embodiments of the plant, the infection-responsive promoter is responsive to filamentous fungal infection. Moreover, in some embodiments of the plant, the infection-responsive promoter is responsive to bacterial infection.

In some embodiments, the transgenic plant of the present invention shows complex disease resistance. In other words, the infection-responsive promoter may be a promoter that is responsive to the infections by a filamentous fungus and a bacterium.

In some embodiments, the transgenic plant of the present invention has agronomic traits that are at least comparable (equivalent) to those of naturally-occurring plants. This is because the infection-responsive promoter does not induce the expression of the WRKY45 gene product in the absence of infection or keeps it at low levels as compared to that after infection.

In another aspect, the present invention provides a progeny or clone of the above transgenic plant. Moreover, in another aspect, the present invention provides propagation material of the above transgenic plant.

In another aspect, the present invention provides an isolated nucleic acid construct comprising a functional WRKY45 gene. In this nucleic acid construct, the WRKY45 gene is operably linked to an infection-responsive promoter and a translational enhancer. Further, in another aspect, the present invention provides a vector comprising this nucleic acid construct, and a plant cell into which this nucleic acid construct or the vector has been introduced.

Moreover, in another aspect, the present invention provides a method of improving plant disease resistance using the above nucleic acid construct or the vector. In one embodiment of this method, the nucleic acid construct or the vector is introduced into a plant. Further, in one embodiment of this method, the nucleic acid construct or the vector is introduced into a cell.

Furthermore, in another aspect, the present invention provides an agent comprising the above nucleic acid construct or vector for improving plant disease resistance.

Furthermore, in another aspect, the present invention provides a method for producing a gene product in a plant in an infection-inducible manner by operably linking a GST promoter to the gene of interest.

BRIEF DESCRIPTION OF THE DRAWINGS

FIG. 5A shows the growth traits of transformants grown in a program-regulated greenhouse in which temperature and humidity are programmed Homozygotes of the T1 generation were cultivated between July and September with temperatures of 32° C. during the day and 26° C. at night. FIG. 5B shows the growth traits of the plants grown in an external-environment-following greenhouse, in which temperature and humidity change following outside conditions. Homozygotes of the T2 generation were cultivated between June and October. FIG. 5C shows the growth traits of the plants grown in the isolation field in Busan, Korea. Homozygotes of the T2 generation were cultivated between June and October.

FIG. 7A shows the GUS staining pattern in the leaves of $P_{PR1b}$-GUS rice after inoculation with compatible *M. oryzae*. FIG. 7B shows temporal patterns of the transcript levels of the PR1b-promoter-driven GUS gene and endogenous PR1b gene in $P_{PR1b}$-GUS rice after inoculation with compatible *M. oryzae*. ● (circles) show the expression of the GUS gene, ▲ (triangles) show the expression of the endogenous PR1b gene. Solid lines indicate the expression after *M. oryzae* inoculation and broken lines the expression after mock treatment.

DETAILED DESCRIPTION

Figure 1:
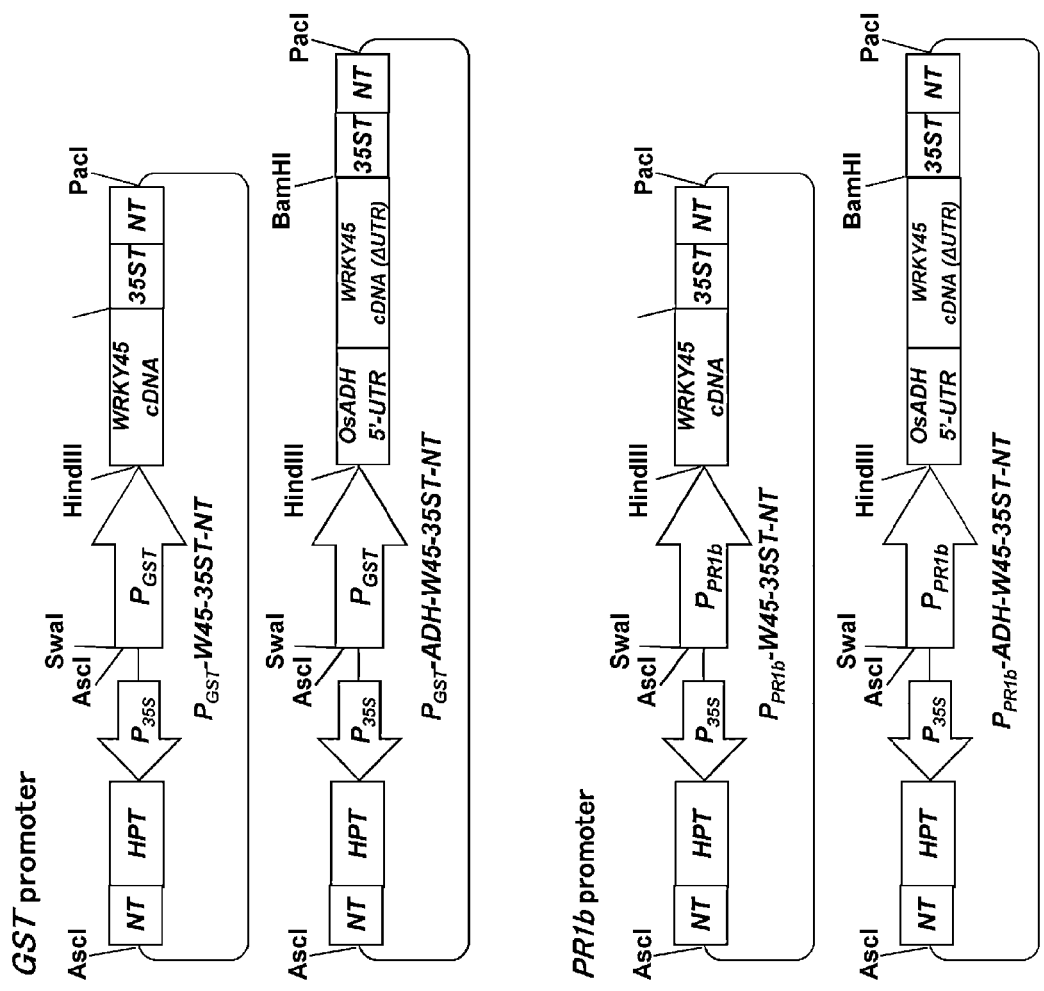
FIG. 1 shows a vector for expressing OsWRKY45 by an infection-responsive promoter. HPT: hygromycin phosphotransferase; NT: nos terminator; 35ST: Cauliflower mosaic virus 35S terminator; $P_{35S}$: Cauliflower mosaic virus 35S promoter; $P_{GST}$: GST promoter; $P_{PR1b}$: PR1b promoter; OsADH 5'-UTR: rice alcohol dehydrogenase gene 5'-untranslated region; ΔUTR: UTR deleted.

As used herein, the singular forms "a", "an", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

The present invention provides plants having disease resistance. More specifically, the present invention provides transgenic plants carrying a functional WRKY45 gene, in which the WRKY45 gene is operably linked to an infection-responsive promoter and a translational enhancer. The WRKY45 gene encodes a plant-derived protein having a function of improving plant disease resistance. The infection-responsive promoter and translational enhancer regulate the expression of WRKY45 gene such that the plant has both disease resistance and acceptable agronomic traits. The transgenic plants of the present invention preferably show complex disease resistance. Moreover, the transgenic plants of the present invention preferably show normal or improved agronomic traits.

Wrky45

The protein expressed from the WRKY45 gene functions as a transcription factor. The WRKY45 gene is preferably derived from a monocot plant, such as wheat (TaWRKY45) and rice (OsWRKY45). It is more preferably derived from a gramineous plant, and even more preferably from a rice plant. The protein produced from a functional WRKY45 gene has a function of improving plant disease resistance. Both disease resistance and acceptable agronomic traits can be achieved by operably linking a functional WRKY45 gene to an infection-responsive promoter and a translational enhancer.

A "functional WRKY45 gene" in the present invention refers to a WRKY45 gene whose gene product has the function of the WRKY45 protein when the gene is expressed in a cell. A "functional WRKY45 gene" has at least a function of improving plant disease resistance. Since the transcription factor encoded by a functional WRKY45 gene functions to improve plant disease resistance, it is possible to generate a plant with pathogen resistance by transforming the plant with a polynucleotide encoding the protein.

A "WRKY45 gene" in the present invention refers to a polynucleotide encoding a WRKY45 transcription factor. In one embodiment, the WRKY45 gene includes a polynucleotide encoding the rice OsWRKY45 transcription factor. The exemplary polynucleotide sequence of the OsWRKY45 transcription factor gene is shown in SEQ ID NO: 1, and the exemplary amino acid sequence of the protein encoded by the polynucleotide is shown in SEQ ID NO: 2.

The aforementioned "functional WRKY45 gene" may have a nucleotide sequence homologous to that of SEQ ID NO: 1. Thus, proteins produced by the "functional WRKY45 gene" may have an amino acid sequence homologous to that of SEQ ID NO: 2. Such proteins having an amino acid sequence homologous to that of SEQ ID NO: 2 may have the function of improving plant resistance to a disease of the present invention. Meanwhile, the "functional WRKY45 gene" may be fused to a heterologous sequence such as a tag or signal peptide. Furthermore, it may also be fused to proteins having other functions.

Accordingly, the "functional WRKY45 gene" of the present invention encompasses polynucleotides encoding proteins that are functionally equivalent to the protein with the amino acid sequence of SEQ ID NO: 2. Such polynucleotides include, for example, polynucleotides encoding proteins comprising an amino acid sequence with high homology to the amino acid sequence of SEQ ID NO: 2. In other words, such polynucleotides include, for example, a polynucleotide encoding a protein consisting of an amino acid sequence having one or more amino acid substitutions, deletions, additions, and/or insertions in the amino acid sequence of SEQ ID NO: 2.

In the present application, "high homology" in an amino acid sequence refers to a sequence identity of at least 50% or higher, preferably 70% or higher, more preferably 90% or higher, or further more preferably 95% or higher (for example, 96%, 97%, 98%, or 99% or higher) in the whole amino acid sequence.

Polynucleotides encoding a protein consisting of an amino acid sequence having one or more amino acid substitutions, deletions, additions, and/or insertions in the amino acid sequence of SEQ ID NO: 2 can be prepared by methods well known to those skilled in the art. Such methods include, for example, the site-directed mutagenesis method. Moreover, a change in the amino acid sequence of a protein due to a mutation in the nucleotide sequence encoding the protein may also occur in nature. Even the polynucleotides which encode a protein having an amino acid sequence with one or more amino acid substitutions, deletions, or additions in the amino acid sequence of natural proteins are included in the polynucleotides encoding proteins that are functionally equivalent to the protein with the amino acid sequence of SEQ ID NO: 2, as long as the polynucleotides encode proteins functionally equivalent to the natural protein (SEQ ID NO: 2). Furthermore, even when nucleotide sequences are mutated, the mutations do not necessarily involve amino acid mutations in proteins (synonymous mutation). Such synonymous mutants are also included in the polynucleotides encoding proteins that are functionally equivalent to the amino acid sequence of SEQ ID NO: 2.

Methods well known to those skilled in the art for preparing polynucleotides encoding proteins functionally equivalent to the transcription factor protein set forth in SEQ ID NO: 2 include methods using hybridization techniques and polymerase chain reaction (PCR) techniques. That is, those skilled in the art can usually isolate polynucleotides highly homologous to the corresponding transcription factor gene from rice and other plants by using the nucleotide sequence (SEQ ID NO: 1) of the transcription factor gene or a portion thereof as a probe, or using an oligonucleotide that specifically hybridizes to the transcription factor gene (SEQ ID NO: 1) as a primer. Such polynucleotides encoding proteins functionally equivalent to a transcription factor protein that can be isolated by hybridization techniques and PCR techniques are also included in the polynucleotides encoding proteins that are functionally equivalent to the amino acid sequence of SEQ ID NO: 2.

In order to isolate such polynucleotides, the hybridization reaction is preferably performed under stringent conditions. Stringent hybridization conditions in the present invention refer to the conditions of 6 M urea, 0.4% SDS, and 0.5×SSC at 65° C. or conditions of similar stringency. Isolation of polynucleotides with higher homology can be expected when using more stringent conditions, for example, conditions of 6 M urea, 0.4% SDS, and 0.1×SSC at 65° C. The DNAs thus isolated are thought to encode a protein with a high homology to the amino acid sequence (SEQ ID NO: 2) of a transcription factor protein on the amino acid level.

Amino acid sequence identity or nucleotide sequence identity can be determined by using the BLAST algorithm developed by Karlin and Altschul (Proc. Natl. Acad. Sci. USA 87:2264-2268, 1990; and Proc. Natl. Acad. Sci. USA 90(12), 5873, 1993). Programs referred to as BLASTN and BLASTX, which are based on the BLAST algorithm, have been developed (Altschul, S. F. et al., J. Mol. Biol. 215:403, 1990). To analyze nucleotide sequences by BLASTN, the parameters are set at, for example, score=100 and word length=12. On the other hand, the parameters used for the analysis of amino acid sequences by BLASTX are set at, for example, score=50 and word length=3. When using the BLAST and Gapped BLAST programs, the default parameters are used for each program. Specific techniques for such analyses are known in the art.

Whether or not a polynucleotide obtained by an above method encodes a protein that functions to improve plant disease resistance can be assessed by the method described below. The most common procedure involves adding a known disease-causing pathogen to a plant introduced with the polynucleotide, and then examining the plant for symptoms during cultivation in a growth chamber. When no disease symptom appears despite addition of the pathogen, it is clear that the introduced polynucleotide encodes a protein having the function of improving plant disease resistance. Suppression or reduction of the disease symptoms can also be interpreted as introduction of a polynucleotide encoding a protein having the function of improving plant disease resistance.

Infection-Responsive Promoter

The promoter used in the present invention is an infection-responsive promoter. An "infection-responsive promoter" is a promoter whose activity increases in response to pathogenic infection. The infection-responsive promoter may also retain some activity in the absence of infection. Examples of an infection-responsive promoter include promoters of the EL5, EF1, hyp2, Cys, GST, HYP3, PR1b, PR1aL, and POX genes. In the present invention, examples of preferable promoters include the rice plant PR1b promoter and the rice plant GST promoter.

In the present invention, an infection-responsive promoter is operably linked to a functional WRKY45 gene. Herein, the phrase "operably linked" means that a protein-encoding polynucleotide is linked to a promoter in such a manner that the expression of the downstream polynucleotide which encodes the protein is induced by the binding of endogenous transcription factors to the promoter. Even if the polynucleotide encoding the protein is fused to another gene, and a fusion protein of the protein with a different gene product is produced, this is included in the meaning of "operably linked" mentioned above, as long as the expression of the fusion protein is induced through the binding of transcription factors to the promoter. For example, the sequences of the promoter and the WRKY45 gene do not need to be directly linked, and other intervening sequences may be present in between these two sequences. In some embodiments of the present invention, a translational enhancer sequence exists in between the infection-responsive promoter sequence and the WRKY45 gene sequence.

Promoters used in the present invention are those having a function of regulating the expression of polynucleotides encoding a plant-derived protein having a function of improving plant disease resistance, so that the plant has both disease resistance and acceptable agronomic traits. In the present invention, a polynucleotide encoding a plant-derived protein having a function of improving plant disease resistance is operably linked downstream of the above-mentioned promoter. Through activation of the above-mentioned promoter, the protein and the polynucleotide encoding the protein can be expressed in plant cells, transgenic plants, or propagation materials of the transgenic plants.

Examples of the rice PR1b promoter include a polynucleotide having the nucleotide sequence of SEQ ID NO: 3, and polynucleotides showing high identity to the polynucleotide having the nucleotide sequence of SEQ ID NO: 3.

Examples of the rice GST promoter include a polynucleotide having the nucleotide sequence of SEQ ID NO: 4, and polynucleotides showing high identity to the polynucleotide having the nucleotide sequence of SEQ ID NO: 4.

"High identity" in a polynucleotide sequence refers to a sequence identity of at least 50% or higher, preferably 70% or higher, more preferably 90% or higher, or even more preferably 95% or higher (for example, 96%, 97%, 98%, or 99% or higher) in the whole nucleotide sequence. Nucleotide sequence identity can be determined using the aforementioned BLAST algorithm or such. A polynucleotide having high identity to a particular polynucleotide sequence can be obtained, for example, by methods that use the aforementioned site-directed mutagenesis method, hybridization technique, or polymerase chain reaction (PCR) technique.

When an infection-responsive promoter of the present invention is used, the expression (transcription) of the polynucleotide operably linked downstream thereof is induced in response to infection. Induction of expression (transcription) occurs preferably in 36 hours or less, more preferably in 24 hours or less, more preferably in 12 hours or less, more preferably in 6 hours or less, more preferably in 3 hours or less, even more preferably in 2 hours or less, most preferably in 1 hour or less, or even most preferably in 30 minutes or less after infection. In particular, when the PR1b promoter is used, it is preferable that only the 2 kb sequence upstream of the PR1b gene is excised and used for early activation of expression.

The activity of the above-mentioned promoters can be examined by those skilled in the art, for example, by well-known reporter assays using reporter genes. The reporter genes are not particularly limited as long as their expression is detectable, and include the CAT gene, lacZ gene, luciferase gene, β-glucuronidase gene (GUS), and GFP gene, which are generally used by those skilled in the art. The expression levels of the reporter genes can be measured by methods well known to those skilled in the art. For example, when the reporter gene is the CAT gene, the expression level of the reporter gene can be measured by detecting the acetylation of chloramphenicol catalyzed by the gene product. When the reporter gene is the lacZ gene, luciferase gene, GUS, or GFP gene, the expression level of the reporter gene can be measured by detecting color development of the pigment compound as a result of the catalytic action of the gene expression product; detecting fluorescence of the fluorescent compound as a result of the catalytic action of the gene expression product; detecting the luminescence of Glucuron (ICN) or color development of 5-bromo-4-chloro-3-indolyl-β-glucuronide (X-Gluc) as a result of the catalytic action of the gene expression product; or detecting the fluorescence of the GFP protein, respectively.

The level of expression of the polynucleotide by the infection-responsive promoter of the present invention can be measured using methods known to those skilled in the art. For example, by extracting mRNA of the gene or polynucleotide of the present invention by a standard method, the level of expression of the gene or polynucleotide mentioned above can be measured by performing an RT-PCR method (for example, a real-time quantitative RT-PCR analysis method) or the northern hybridization method.

Translational Enhancer

In the present invention, "translational enhancer" refers to a polynucleotide which increases the productivity of gene product (i.e., protein), in gene expression. In the present invention, the translational enhancer is operably linked to a functional WRKY45 gene. Herein, "operably linked" means that the translational enhancer is linked to a polynucleotide encoding a protein so as to increase the translation efficiency of the transcription product encoding the protein. For example, sequences of the translational enhancer and the WRKY45 gene do not need to be directly linked, and other intervening sequences may be present in between.

Examples of a translational enhancer used in the present invention include the 5'-untranslated region of the alcohol dehydrogenase (ADH) gene (ADH-UTR) of rice, tobacco ADH-UTR, and *Arabidopsis* ADH-UTR; however, rice ADH-UTR is preferred. More specifically, examples of a translational enhancer of the present invention include a polynucleotide having the nucleotide sequence of SEQ ID NO: 5, and polynucleotides showing high identity to the polynucleotide having the nucleotide sequence of SEQ ID NO: 5.

High identity in a polynucleotide sequence refers to a sequence identity of at least 50% or higher, preferably 70% or higher, more preferably 90% or higher, or even more preferably 95% or higher (for example, 96%, 97%, 98%, or 99% or higher) in the whole nucleotide sequence. Nucleotide sequence identity can be determined using the aforementioned BLAST algorithm or such.

In the present invention, the translational enhancer is used in combination with the infection-responsive promoter. A particularly preferable combination is the combination of the rice PR1b promoter and the rice ADH-UTR, or the combination of the rice GST promoter and the rice ADH-UTR.

Terminator

In the present invention, "terminator" refers to a transcription termination sequence. Examples of a terminator of the present invention include the 35S terminator (35ST) of the Cauliflower mosaic virus (CaMV) and the terminator of the Nopaline synthase (Nos) gene (NT).

In the present invention, one terminator may be used alone. Alternatively, a tandem terminator in which two terminators are linearly linked may be used, and a tandem terminator is preferably used. In one embodiment, such a tandem terminator is operably linked to the WRKY45 gene. Herein, "operably linked" means that the tandem terminator is linked to a polynucleotide encoding the protein such that termination of transcription of the polynucleotide is promoted. For example, sequences of the terminator and the WRKY45 gene do not need to be directly linked, and other intervening sequences may be present in between these sequences.

An example of a tandem terminator used in the present invention includes a tandem terminator in which 35ST and NT are linked. More specifically, examples of a terminator of the present invention include a polynucleotide having the nucleotide sequence of SEQ ID NO: 6, and polynucleotides showing high identity to the polynucleotide having the nucleotide sequence of SEQ ID NO: 6. Herein, high identity in a polynucleotide sequence refers to a sequence identity of at least 50% or higher, preferably 70% or higher, more preferably 90% or higher, or even more preferably 95% or higher (for example, 96%, 97%, 98%, or 99% or higher) in the whole nucleotide sequence. Nucleotide sequence identity can be determined using the aforementioned BLAST algorithm or such.

In the present invention, when expressing a polynucleotide using a promoter and a translational enhancer, a terminator may or may not be used; however, a terminator is preferably used in combination with the promoter and translational enhancer. In an embodiment, a tandem terminator in which 35ST and NT are linked is used in combination with rice ADH-UTR. More preferably, a tandem terminator in which 35ST and NT are linked is used in combination with a PR1b promoter or GST promoter and an ADH-UTR translational enhancer.

Plant Disease

In the present invention, the phrase "plant disease" refers to any physiological disorder in plants caused by pathogens such as filamentous fungi (mainly molds), bacteria, or viruses, and which may reduce agricultural production and damage ecological environment. Pathogens are not particularly limited, and in addition to the aforementioned three pathogens, diseases caused by actinomycetes, algae, phytoplasma (plant pathogenic microorganism), and such also exist. In the present invention, "plant disease" may also be referred to as "plant infection".

Hereinafter, three typical disease-causing pathogens in plants (filamentous fungi, bacteria, and viruses), and symptoms of the diseases caused by these pathogens are described. Although a "disease" in the present invention is not particularly limited, it may be any one of the diseases described below. Further, a "disease" may also be referred to as an "infection" in the present invention.

Filamentous fungi are microorganisms composed of multicellular "hyphae" and proliferate by forming spores. Since they have a rigid cell wall made of chitin, they are considered to be highly resistant to drugs. Based on their shape and characteristics, filamentous fungi are classified into Phycomycetes (molds), Deuteromycetes (molds), Ascomycetes (molds/mushrooms), and Basidiomycetes (mushrooms). Phycomycetes are further divided into Mastigomycotinas and Zygomycetes.

Diseases caused by filamentous fungi present a variety of symptoms, including blotch formation on stem and leaf, rot, induction of dieback by impairing base of aerial part or root, formation of swellings such as gal, etc. As a major symptomatic tendency in diseases caused by filamentous fungi, growth of powdery molds and formation of granular black substances (sclerotia=mass of hyphae) are often observed in the affected sites. The typical filamentous fungal disease in rice plants includes diseases caused by *Pseudocochliobolus lunatas, Rhizoctonia oryzae-sativae, Sclerophthora macrospora, Metasphaeria albescens, Waitea circinata, Dreschslera gigantea, Entyloma dactylidis, Bipolaris oryzae, Chromelosporium fulvum, Magnaporthe salvinii, Peziza ostracoderma, Tilletia barclayana*, and *Rhizoctonia oryzae*. Rice blast disease, a model disease in the Examples, is also a filamentous fungous disease; however, filamentous fungous diseases are not limited to this disease.

Bacteria are microorganisms composed of a single cell that have various shapes according to the species. Bacteria move in water by swimming, and invade plant bodies through wounds formed on the stub, stomata on the underleaf, etc. Bacterial diseases include rotten stem and leaf, induction of an acute dieback, formation of a tumorous swelling, etc. A common symptom includes a somewhat blurred contour of a blotch and yellowish discoloration in its periphery. Typical bacterial diseases in rice include rice bacterial brown stripe, rice bacterial leaf blight, rice bacterial palea browning, rice bacterial grain rot, and rice bacterial seedling blight. Rice bacterial leaf blight, a model disease in the Examples, is also a bacterial disease; however, bacterial diseases are not limited to this disease.

Viruses are basically composed of nucleic acids and proteins, and have various shapes depending on the species. Viruses have only either one of DNA or RNA, and cannot proliferate unless they invade cells of other organisms and utilize their nucleic acid synthesis/protein synthesis functions. Also known are viroids which resemble virus in characteristics and cause similar diseases. Viroids contain only RNAs and have no proteins in their nucleic acid portion, and they are smaller than viruses in size. Diseases caused by viruses and viroids are, in most cases, accompanied by mosaic symptoms having pale patchy patterns in leaves and flowers, malformations such as dwarf and deformation, small brown necrotic spots, and such. In addition, the whole plant may become yellow and dwarf, resulting in a significant growth inhibition. Typical viral diseases in rice include rice black-streaked dwarf, rice transitory yellowing disease, and rice dwarf disease.

Improved Resistance

In the present invention, to "improve plant disease resistance" includes conferring a plant with a trait/effect in which symptoms of the aforementioned diseases do not occur or hardly occur by expressing the nucleic acid construct of the present invention in the plant. This phrase also indicates a trait/effect of improving resistance to pathogens and reducing their infection.

The effect of improving disease resistance may last throughout the plant lifetime or may be expressed for a certain period of time (for example, only at the early growth stage). In addition, the disease resistance may be towards a plurality of pathogens or only a specific pathogen. In the present invention, "complex disease resistance" refers to a trait in which symptoms of a plurality of plant diseases caused by plant pathogens such as filamentous fungi, bacteria, and viruses do not occur or hardly occur. In some embodiments, the plants of the present invention show resistance to at least rice blast and bacterial leaf blight.

Improved Agronomic Traits

In the present invention, to "improve the agronomic traits of a plant" includes conferring a plant with a trait/effect such that a delay in the plant growth or a decrease in the yield of propagation materials (seeds) of the plant does not occur or hardly occur when a nucleic acid construct of the present invention is expressed in the plant. An agronomic trait in the present invention refers to plant height, fresh weight, panicle number, seed number, seed weight, tiller number, fertility, etc. "Normal or improved agronomic traits" indicate that these traits are maintained or improved as compared with plants into which the WRKY45 gene has not been introduced.

Evaluation of the agronomic traits mentioned above can be carried out, for example for the panicles and culms of rice plants by planting or seeding transgenic gramineous plants or T1 or T2 seeds obtained by self-pollination of the transgenic gramineous plants in a suitable growth medium or soil, growing them under long-day conditions (day/night: 16 hour/8 hour day length) at 20° C. to 30° C., and then examining the number, sizes, shapes, and such of the panicles and culms (for example, tillers). Furthermore, the inflorescence, cariopsides, seeds, grains, unhulled rice kernels, and rice grains of rice plants can be evaluated by planting or seeding transgenic gramineous plants or T1 or T2 seeds obtained by self-pollination of the transgenic gramineous plants in a suitable growth medium or soil, growing them under long-day conditions (day/night: 16 hour/8 hour day length) at 20° C. to 30° C., and then examining the number, size, shape, and such of the inflorescence, cariopsides, seeds, grains, unhulled rice kernels, and rice grains. Cultivation of plants can be carried out in a closed-system or a non-closed-system greenhouse, a growth chamber (with completely artificial light), an external-environment-following glass greenhouse in which the temperature and humidity change following outside conditions, or an experimental isolation field.

Comparable or Improved Agronomic Trait

In the present invention, the phrase "to have both disease resistance and an acceptable agronomic trait(s) of the plant" means that the plant has the above-mentioned disease resistance (properties showing improved resistance to a disease), and at the same time, has a comparable or even improved agronomic trait compared to that of a naturally-occurring plant, or a wild-type plant. In the present invention, having "a comparable or improved agronomic trait compared to that of a naturally-occurring plant" means that the size, total weight, number, and such of organs (tissues) of plants such as panicles, culms, seeds, unhulled kernels, rice grains, cariopsides, tillers, and spicules, are comparable to or increased relative to those of a naturally-occurring plant. Furthermore, in the present invention, having "a comparable or improved agronomic trait compared to that of a naturally-occurring plant" means that a trait relating to the organs (tissues) (for example, the number and size of panicles and culms of rice, maize, and such, and the number and size, as well as the variation in shape, and color, and such of the seeds (endosperm) of rice, maize, and such) is equivalent or improved.

Figure 4:
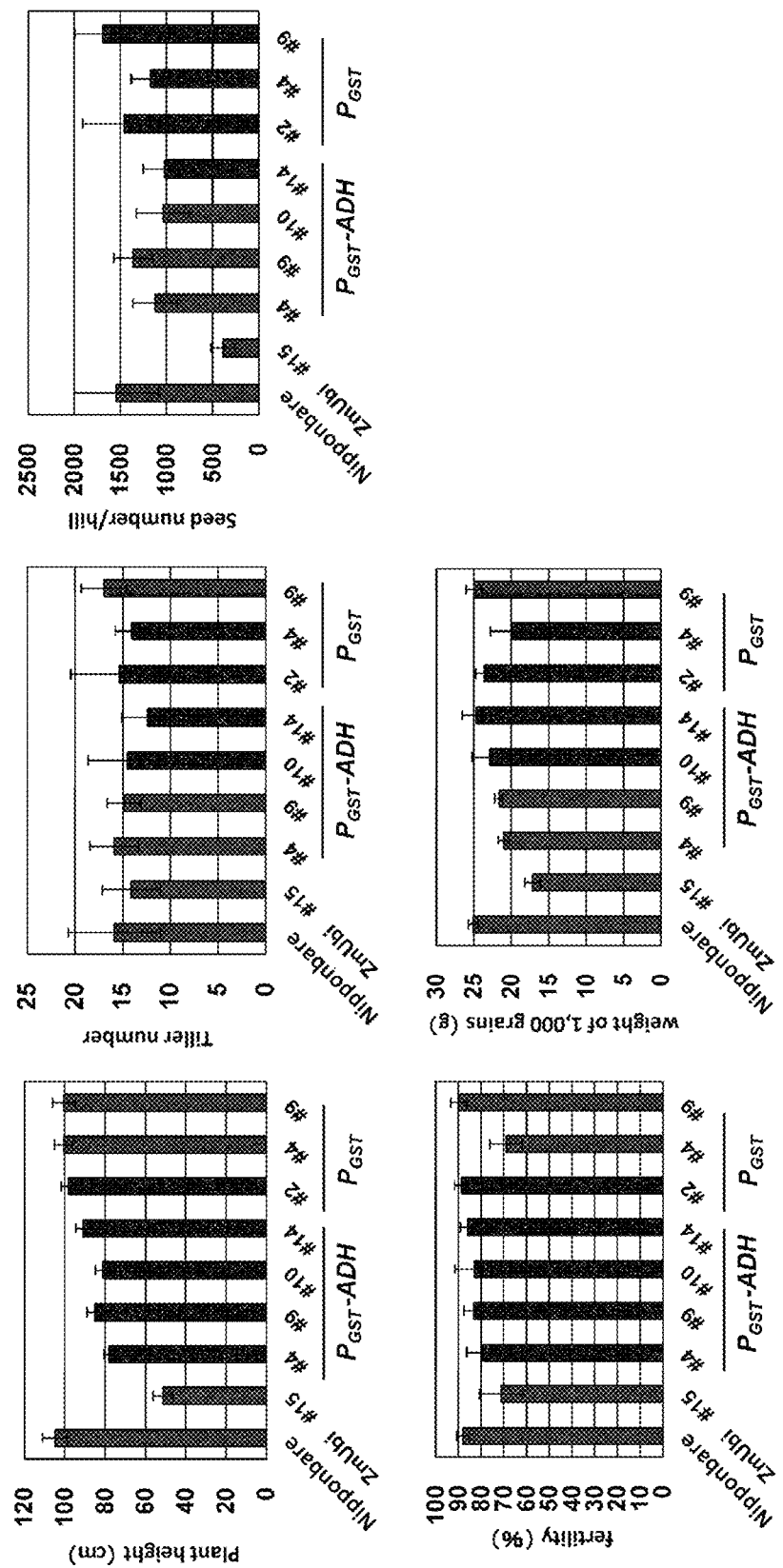
FIG. 4 shows the growth traits of rice lines expressing OsWRKY45 through the GST promoter in an isolation field in Korea. Homozygotes of the T2 generation were used. They were cultivated in the isolation field between June and October in Busan, Korea.

Whether a plant has "a comparable or improved agronomic trait compared to that of a naturally-occurring plant" can be judged as a whole after each trait is evaluated. For example, as shown in FIG. 4, rice carrying the OsWRKY45 gene operably linked to the $P_{GST}$ promoter, ADH-UTR translational enhancer, and tandem terminator may have an overall plant height than that of Nipponbare; however, numerical values close to those of Nipponbare are obtained with other traits, so that as a whole, the agronomic traits can be said to be comparable to those of the naturally-occurring plant. The plants of the present invention may also contain other genetic modifications that improve the agronomic traits. For example, the plants of the present invention can contain genetic modifications that increase the plant height. In some embodiments, the plants of the present invention show agronomic traits that are at least comparable to those of naturally-occurring plants. In other words, in some embodiments, the plants of the present invention show normal or improved agronomic traits.

Plant

Examples of a "plant" in the present invention include a monocot plant and a dicot plant. Examples of a monocot plant include maize, wheat, barley, rye, rice, sorghum, and grass; and examples of a dicot plant include cotton, sugar beet, peanut, potato, sunflower, soybean, alfalfa, and rapeseed. In the present invention, plants which develop a disease are not particularly limited; however, they are preferably monocot plants, more preferably gramineous plants, and more preferably rice plants.

Nucleic Acid Construct

The present invention provides a transgenic plant comprising a polynucleotide encoding a plant-derived protein having a function of improving resistance of an aforementioned plant to a disease. More specifically, the protein is a WRKY45 transcription factor.

In the present invention, a "transgenic plant comprising a polynucleotide encoding a plant-derived protein having a function of improving plant disease resistance" is a plant carrying a polynucleotide encoding a plant-derived protein having a function of improving plant disease resistance, more specifically, a polynucleotide encoding a WRKY45 transcription factor. The plant of the present invention carries a polynucleotide encoding a plant-derived protein having a function of improving plant disease resistance, and a promoter and translational enhancer having the function of regulating the expression of the polynucleotide such that the plant has both disease resistance and acceptable agronomic traits. The plant may further comprise a terminator, and the terminator may be a tandem terminator.

In the present invention, a "transgenic plant comprising a polynucleotide encoding a plant-derived protein having a function of improving plant disease resistance" may be a plant carrying a nucleic acid construct comprising a polynucleotide encoding a plant-derived protein having a function of improving plant disease resistance, and a promoter and translational enhancer having the function of regulating the expression of the polynucleotide such that the plant has both disease resistance and acceptable agronomic traits. The nucleic acid construct may be contained in a vector. The transgenic plants of the present invention have improved pathogen resistance as compared to wild-type plants.

In such a nucleic acid construct, a functional WRKY45 gene is operably linked to an infection-responsive promoter and a translational enhancer. The WRKY45 gene is preferably the rice OsWRKY45 transcription factor. The infection-responsive promoter is preferably the rice PR1b gene promoter or rice GST gene promoter. The translational enhancer is preferably the 5'-untranslated region sequence of rice alcohol dehydrogenase. Moreover, the nucleic acid construct may contain a terminator, and the terminator may be a tandem terminator. Further, the nucleic acid construct may be an isolated nucleic acid construct. The nucleic acid construct is not particularly limited; however, it may function for example as an expression cassette. The nucleic acid construct of the present invention can be used, for example, for preparing recombinant proteins or for generating transgenic plants (transformed plants) with improved resistance to diseases.

Vectors

The present invention also provides vectors into which the above-described nucleic acid constructs of the present invention have been inserted. The vectors of the present invention include, in addition to vectors used for producing recombinant proteins, vectors for expressing the nucleic acid constructs of the present invention in plant cells so as to produce transgenic plants. Such vectors are not particularly limited and include, for example, "pBI121", "pBI221", and "pBI101" plasmids (all from Clontech). These vectors include a terminator sequence having a polyadenylation site required for stabilization of the transcription products. Vectors used for plant cell transformation are not particularly limited as long as they can express the inserted gene in the cells. Herein, "plant cells" include plant cells in various forms, for example, suspended cultured cells, protoplasts, leaf segments, and calluses. The vectors of the present invention can be used, for example, for preparing recombinant proteins or for generating transgenic plants (transformed plants) with improved resistance to diseases.

Progenies and Clones

The present invention provides progenies and clones of the transgenic plants of the present invention, as well as propagation materials of the transgenic plants of the present invention. Once a transgenic plant of the present invention is obtained, it is possible to obtain its progeny from the plant by sexual or asexual reproduction, or its clones using known methods. It is also possible to obtain propagation materials (such as seeds, fruits, panicles, tubers, root tubers, stubs, calluses, and protoplasts) from the plant and its progenies or clones, and to mass-produce the plant based on these materials.

The present invention provides transformed cells into which the above-described nucleic acid constructs or vectors inserted with the nucleic acid constructs of the present invention have been introduced. Cells into which the nucleic acid constructs or vectors of the present invention are introduced include, in addition to the above-described cells used for producing recombinant proteins, plant cells for producing transgenic plants. Plant cells are not particularly limited, and include, for example, cells of rice, *Arabidopsis*, corn, potato, and tobacco. Plant cells of the present invention include, in addition to cultured cells, cells in plants as well as protoplasts, shoot primordia, multiple shoots, and hairy roots. The nucleic acid constructs or vectors can be introduced into plant cells using various methods known to those skilled in the art, such as the polyethylene glycol method, electroporation method, *Agrobacterium*-mediated method, and particle gun method.

The present invention also provides plants (transgenic plants) regenerated from transformed cells into which nucleic acid constructs or vectors of the present invention have been introduced. Regeneration of a plant from transformed plant cells can be performed by methods known to those skilled in the art according to the type of plant cell. For example, in rice, several techniques for producing transgenic plants have been already established, and they include a method for introducing a gene into a protoplast with polyethylene glycol to regenerate a plant (suitable for indica rice varieties); a method for introducing a gene into a protoplast with electrical pulse to regenerate a plant (suitable for japonica rice varieties); a method for directly introducing a gene into a cell by the particle gun method to regenerate a plant; a method for introducing a gene into a cell via *Agrobacterium* to regenerate a plant, and such. These methods are widely used in the technical field of the present invention. In this invention, these methods can be preferably used.

Transformed plant cells can regenerate plants by redifferentiation. Methods for redifferentiation vary depending on the type of plant cell. The methods include, for example, the method of Fujimura et al. (Plant Tissue Culture Lett. 2: 74 (1995)) for rice; method of Shillito et al. (Bio/Technology 7: 581 (1989)) and method of Gorden-Kamm et al. (Plant Cell 2: 603 (1990)) for corn; method of Visser et al. (Theor. Appl. Genet 78: 594 (1989)) for potato; method of Nagata and Takebe (Planta 99: 12 (1971)) for tobacco; method of Akama et al. (Plant Cell Reports 12: 7-11 (1992)) for *Arabidopsis*; and method of Dohi et al. (JP-A (Kokai) H08-89113) for eucalyptus.

Method for Producing Transgenic Plants

The present invention provides a method for producing a transgenic plant, which includes the steps of: a) introducing into a plant cell a nucleic acid construct comprising a polynucleotide encoding a plant-derived protein having a function of improving plant disease resistance; and b) regenerating a plant from the plant cell. The nucleic acid construct may be contained in a vector. More specifically, the nucleic acid construct contains a functional WRKY45 gene operably linked to an infection-responsive promoter and a translation enhancer. The WRKY45 gene is preferably the gene of the rice OsWRKY45 transcription factor. The infection-responsive promoter is preferably the rice PR1b gene promoter or the rice GST gene promoter. The translational enhancer is preferably the 5'-untranslated region sequence of the rice alcohol dehydrogenase.

To produce transgenic plants (transformed plants) having improved plant disease resistance using the nucleic acid constructs of the present invention, the nucleic acid constructs of the present invention are inserted into appropriate vectors, and then the vectors are introduced into plant cells to regenerate transformed plant cells. The polynucleotide encoding the transcription factor WRKY45 has the function of improving plant disease resistance, and it is possible to introduce a nucleic acid construct containing this polynucleotide into an arbitrary plant variety and regulate its expression using a promoter, thereby improving disease resistance in that variety.

In the method for producing a transgenic plant of the present invention, the nucleic acid constructs or vectors can be introduced into plant cells using various methods known to those skilled in the art, such as the polyethylene glycol method, electroporation method, *Agrobacterium*-mediated method, and particle gun method.

In the method for producing a transgenic plant of the present invention, regeneration of a plant from a plant cell can be carried out by methods known to those skilled in the art depending on the type of plant cell as described above.

Based on the method for producing a transgenic plant of the present invention, plants having both disease resistance and acceptable agronomic traits can be produced. The plants having improved disease resistance thus produced have improved pathogen resistance compared to wild-type plants. The method may also confer complex disease resistance on the treated plant. Use of the techniques of the present invention enables pesticide-free production of rice, which is a useful agricultural product, and may lead to prevention of environmental destruction and improved productivity.

This transformation (introduction of a nucleic acid construct or vector into a plant cell) requires an extremely short period of time compared to the conventional gene transfer by crossing, and is advantageous in that no alteration of other characteristics occurs.

Method for Improving Resistance

The present invention provides a method for improving plant disease resistance, including the step of introducing into the plant a nucleic acid construct comprising a polynucleotide encoding a plant-derived protein having a function of improving plant disease resistance. The nucleic acid construct may be contained in a vector. More specifically, the nucleic acid construct contains a functional WRKY45 gene operably linked to an infection-responsive promoter and a translation enhancer. The WRKY45 gene is preferably the gene of the rice OsWRKY45 transcription factor. The infection-responsive promoter is preferably the rice PR1b promoter or the rice GST promoter. The translational enhancer is preferably the 5'-untranslated region sequence of the rice alcohol dehydrogenase.

In the present invention, in the methods for improving plant disease resistance, introduction into a plant of a nucleic acid construct containing a polynucleotide encoding a plant-derived protein having a function of improving plant disease resistance can be carried out using an aforementioned method of introducing the nucleic acid construct into a plant cell.

By using the methods for improving plant disease resistance of the present invention, plants having improved or enhanced pathogen resistance compared to wild-type plants can be obtained. Moreover, by using the methods for improving plant disease resistance of the present invention, plants having both disease resistance and acceptable agronomic traits can be obtained. The method may also confer complex disease resistance on the treated plant. Use of the techniques of the present invention enables pesticide-free production of rice, which is a useful agricultural product, and may lead to prevention of environmental destruction and improved productivity.

Agents for Improving Resistance

The present invention provides agents for improving plant disease resistance, which contain a polynucleotide encoding a plant-derived protein having a function of improving plant disease resistance.

The agents of the present invention are agents containing an above-described nucleic acid construct as an active ingredient, and have an effect of improving plant disease resistance. More specifically, the nucleic acid construct contains a functional WRKY45 gene operably linked to an infection-responsive promoter and a translation enhancer. The WRKY45 gene is preferably the gene of the rice OsWRKY45 transcription factor. The infection-responsive promoter is preferably the rice PR1b gene promoter or rice GST gene promoter. The translational enhancer is preferably the 5'-untranslated region sequence of the rice alcohol dehydrogenase. The nucleic acid construct in the agents may be incorporated in a vector.

In the agents of the present invention, sterilized water, physiological saline, vegetable oil, surfactants, lipids, solubilization agents, buffers, preservatives, and such may be mixed in as necessary, in addition to the active ingredients, i.e., nucleic acid constructs or vectors.

By using the agents of the present invention, plants having improved or enhanced pathogen resistance as compared to wild-type plants can be obtained. Moreover, by using the agents of the present invention, plants having both disease resistance and acceptable agronomic traits can be obtained. The agents may also confer complex disease resistance on the treated plant. Use of the agents of the present invention enables pesticide-free production of rice, which is a useful agricultural product, and may lead to prevention of environmental destruction and improved productivity.

Use of GST Gene Promoter

Further, the present invention provides a method for producing a gene product in a plant in an infection-inducible manner, including the step of providing a plant having a gene of interest operably linked to a GST promoter. In this method, the GST promoter directs transcription of the gene of interest upon infection to produce the gene product. Examples of the GST promoter include a polynucleotide having the nucleotide sequence of SEQ ID NO: 4, and polynucleotides showing high identity to the polynucleotide having the nucleotide sequence of SEQ ID NO: 4 described above.

In the method of the present invention for producing a gene product in a plant in an infection-inducible manner, a "gene product" is a product produced by transcription or translation of the gene, and is for example, an RNA or a protein.

In the method of the present invention for producing a gene product in a plant in an infection-inducible manner, "infection-inducible manner" refers to induction in response to pathogenic infection.

In the method of the present invention for producing a gene product in a plant in an infection-inducible manner, a "gene of interest" may be any gene, and is preferably a gene encoding a transcription factor, more preferably a gene encoding the transcription factor WRKY, more preferably a gene encoding the transcription factor WRKY45, and even more preferably a gene encoding OsWRKY45.

In the method for producing a gene product in a plant in an infection-inducible manner of the present invention, a promoter which "directs transcription of the gene of interest upon infection" refers to a promoter which shows activity in response to pathogenic infection. More specifically, expression (transcription) of the gene of interest operably linked downstream of the promoter occurs in response to infection by a pathogen. Moreover, when transcription of the gene of interest is induced in response to infection in this way, the product of the gene of interest is produced. Meanwhile, some activity may also be retained in the absence of infection.

A gene product produced using a method of the present invention for producing a gene product in a plant in an infection-inducible manner can be quantified using a method known to those skilled in the art. For example, when the gene product is an mRNA, mRNAs can be extracted by a standard method and the expression level of the gene of interest can be measured by performing an RT-PCR method (for example, the real-time quantitative RT-PCR analysis method) or the northern hybridization method using the mRNAs as template. When the gene product is a protein, proteins can be extracted by a standard method and the expression level of the gene of interest can be measured by performing an SDS-PAGE, Western Blotting, or the like using the protein as target.

By using a method of the present invention for producing a gene product in a plant in an infection-inducible manner, it is possible to produce the product of an arbitrary gene in a plant in a pathogenic infection-inducible manner. Further, when the gene product of the polynucleotide of the present invention encoding a plant-derived protein having a function of improving plant disease resistance is produced in a plant using the present production method, plants having both disease resistance and acceptable agronomic traits can be obtained.

Food and Drink Compositions

Furthermore, the present invention provides food and drink compositions and processed products comprising the aforementioned transgenic plants or propagation materials of the present invention. Examples of the propagation materials of the plants of the present invention (for example, rice plants) include rice. The rice of the present invention can have the same uses as ordinary rice. For example, the rice itself can have edible use by subjecting it to treatments such as cooking, boiling, frying, steaming, or deep-frying. Furthermore, it can be used in combination with food and drink compositions other than rice. For example, it can be used in takikomi gohan (seasoned rice and cooked with meat, fish, and/or vegetables), zosui (rice soup with meat, fish, and/or vegetables), fried rice, and such. Furthermore, rice can be ground and used as a process material for rice flour, glutinous rice flour, udon noodles, soba noodles, spaghetti, macaroni, rice vermicelli, bread, rice snacks such as rice crackers, arare crackers (grilled pieces of rice cakes), cookies, and the like. Furthermore, it may be used as a material for extracting rice oil and such. It can also be used as a raw material for brewing, fermentation, or such. Rice bran may also be used for the purpose of pickling food and drink products. Needless to say, the transgenic plants or propagation materials of the present invention may be used not only for humans, but also as animal feeds (for example, pet food). Furthermore, the food and drink compositions and processed products may be packaged in containers. For example, food and drink products that are packaged in containers such as plastic-molded containers or containers such as retort pouches, sealed, and then sterilized are included in the present invention. That is, the purpose and method of using the transgenic plants or propagation materials of the present invention are not particularly limited.

All Documents Cited Herein are Incorporated by Reference in their Entirety.

EXAMPLES

The following examples are provided by way of illustration only and not by way of limitation. Those skilled in the art can readily recognize the non-critical parameters that could be changed or modified to yield essentially the same or similar results.

Example 1

Generation of Rice Expressing OsWRKY45 by an Infection-responsive Promoter

A vector for expressing OsWRKY45 in a pathogen infection-responsive manner in plants was generated by the following procedure. First, the vector pZH1 was digested with HindIII-PacI, and then a SfiI-PacI fragment containing the OsWRKY45 cDNA and Nos terminator derived from pZH1-Ubi-W45-NT (Shimono, M. et al., Plant Cell, 19:2064 (2007)) as well as a complementary oligo DNA (prepared by annealing a top strand (AGCTTGGCCAAAT; SEQ ID NO: 7) and a bottom strand (TGGCCA; SEQ ID NO: 8)) were inserted into the vector to construct pZH1-W45-NT-1. This was digested with HindIII, and a complementary oligo DNA (prepared by annealing a top strand (AGCTGGCGCGCCATTTAAATA; SEQ ID NO: 9) and a bottom strand (AGCTTATTTAAATGGCGCGCC; SEQ ID NO: 10)) was inserted into the digested vector for construction of pZH1-W45-NT-2.

To obtain infection-responsive promoters from rice, the expression profiles of rice genes following inoculation of rice with *M. oryzae* and Xoo were analyzed by microarray, and nine genes that were responsive to infection by both pathogens (EL5, EF1, hyp2, Cys, GST, HYP3, PR1b, PR1aL, and POX) were selected. Based on the database information (RAP-DB), sequences of approximately 2 kb upstream from the translation initiation site of these genes were amplified by PCR and inserted into HindIII-digested pZH1-W45-NT-2 using the In-Fusion kit (TaKaRa BIO Inc) to construct $P_X$-W45-NT (X represents the name of an aforementioned gene). Then, PCR-amplified 35S terminator sequence was inserted into BamHI-digested $P_X$-W45-NT using the In-Fusion kit so as to obtain a tandem terminator, yielding $P_X$-W45-35ST-NT. The OsWRKY45 cDNA sequence without 5' UTR and 3' UTR sequences (ΔUTR), and the 5'-UTR sequence of the rice alcohol dehydrogenase (OsADH) gene (Sugio T. et al., J. Biosci. Bioeng., 105:300 (2008)) were amplified by PCR and inserted into the HindIII- and BamHI sites of $P_X$-W45-35ST-NT, respectively, using the In-Fusion kit to construct $P_X$-ADH-W45-35ST-NT. $P_{PR1b}$ promoter-based and $P_{GST}$ promoter-based OsWRKY45 expression vectors (with and without the translation enhancer) are shown in FIG. 1.

These OsWRKY45 expression vectors were introduced into Nipponbare rice using the *Agrobacterium* method to obtain transformants.

Example 2

Rice Blast Inoculation Test

To test rice blast resistance, seeds of non-transformants and of the Os WRKY45-expressing rice (T1 generation) were aseptically seeded on an MS medium and an MS medium containing 30 μg/ml hygromycin, respectively. The seeds were kept at 30° C. for five days to germinate, transferred to soil (Bonsol No. 2), and grown for 13 days in a greenhouse. Spores of blast fungus (*M. oryzae* race 007, $1.0 \times 10^5$ spores/mL) were spray-inoculated to the rice seedlings (five-leaf stage), and seven days later, the number of lesions in ten-centimeter regions (in length) around the center of the fifth leaves was counted.

Example 3

Bacterial Leaf Blight Inoculation Test

To test bacterial leaf blight resistance, seeds of non-transformants and of the Os WRKY45-expressing rice (T1 generation) were aseptically seeded on an MS medium and an MS medium containing 30 μg/mL of hygromycin, respectively. The seeds were kept at 30° C. for five days to germinate, transferred to soil (Bonsol No. 2), and grown for 30 days in a greenhouse. Then, leaf-clipping inoculation of the bacteria Xoo was carried out by cutting the tip of the leaves using surgical scissors soaked in a suspension ($OD_{600}=0.03$) of Xoo (T7174 strain). Two weeks after the inoculation, the lengths of the lesions from the inoculated sites were measured.

Example 4

Evaluation of Growth and Yield

To evaluate the agronomic traits of the transformants, homozygote transformants of the T1 or T2 generation were cultivated in a program-regulated glass greenhouse and an external-environment-following glass greenhouse in which the temperature and humidity change following outside conditions. Rice seedlings approximately three weeks after germination were transferred to soil (Bonsol No. 2) in pots, and cultivated in the room with pot rotation twice a week. After growth, the plant height, fresh weight, effective tiller number, seed yield, and fertility rate were examined. When evaluating the growth and yield of the T1 generation, the segregation ratio of the hygromycin-resistant progeny was examined for the collected seeds to check the homo/heterozygosity of their parental plants, and only results of the homozygotes were considered.

Similar surveys of growth and yield were carried out in an isolation field that is not open to the public in Korea (Busan) using T2 generation homozygote lines.

Example 5

Analysis of the Infection Responsiveness of the $P_{PR1b}$ Promoter Using the GUS Gene To analyze the $P_{PR1b}$ promoter activity using the GUS reporter gene, the OsWRKY45 cDNA sequence was excised from $P_{PR1b}$-W45-355T-NT using the restriction enzymes BamHI and HindIII (partial). The coding sequence of the *Escherichia coli*-derived fl-glucuronidase (GUS) gene amplified by PCR using the plasmid pSMAHdN627-M2GUS as template was inserted using the In-Fusion kit (TaKaRa BIO Inc) to generate a vector containing the $P_{PR1b}$ promoter:GUS fusion gene. This vector was introduced into Nipponbare rice by the *Agrobacterium*-mediated method, and the transformants obtained were used for analysis.

Example 6

Analysis of the Transcript Level of the Introduced OsWRKY45 Gene

To analyze the transcript level of the introduced OsWRKY45 gene, RNA was extracted from the fourth leaves of rice at the four-leaf stage before and after inoculation with *M. oryzae*, and analyzed by real-time RT-PCR using the following primers: Forward 5'-TGTGT-GACAAGCAAGAGAAGAGGA-3' (SEQ ID NO: 11), and Reverse 5'-AACGATCGGGGAAATTCGAG-3' (SEQ ID NO: 12). This set of primers only detects OsWRKY45 transcripts derived from the introduced gene.

Example 7

Results of the Rice Blast Inoculation Test

Figure 2:
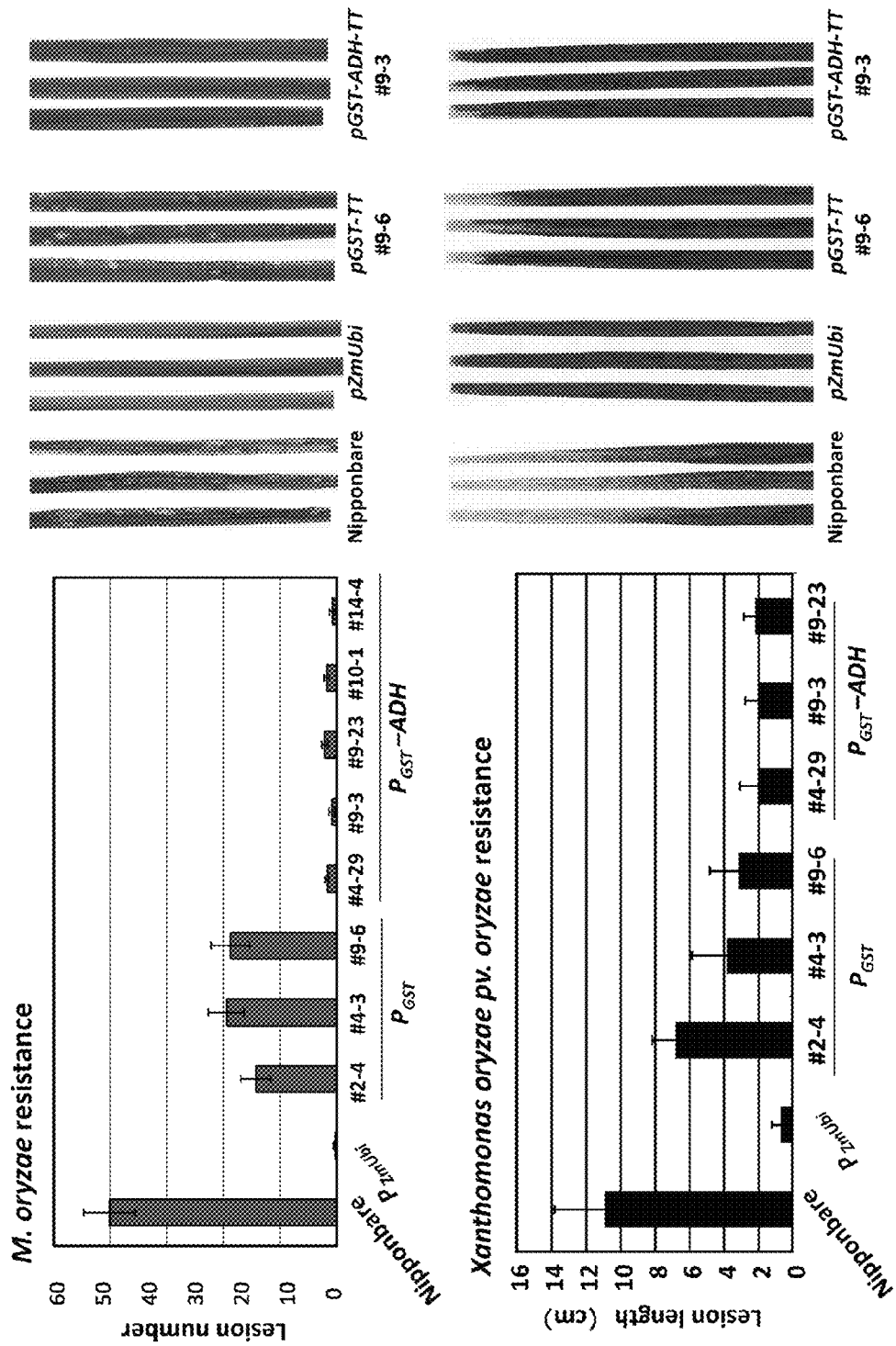
FIG. 2 shows resistance of rice lines expressing OsWRKY45 by the GST promoter against rice blast and bacterial leaf blight diseases. All lines used were homozygotes of the T2 generation. They were assayed for the resistance to rice blast (*Magnaporthe oryzae*) and bacterial leaf blight (Xoo) diseases. $P_{Zmubi}$: maize ubiquitin promoter; TT: tandem terminator.
Figure 3:
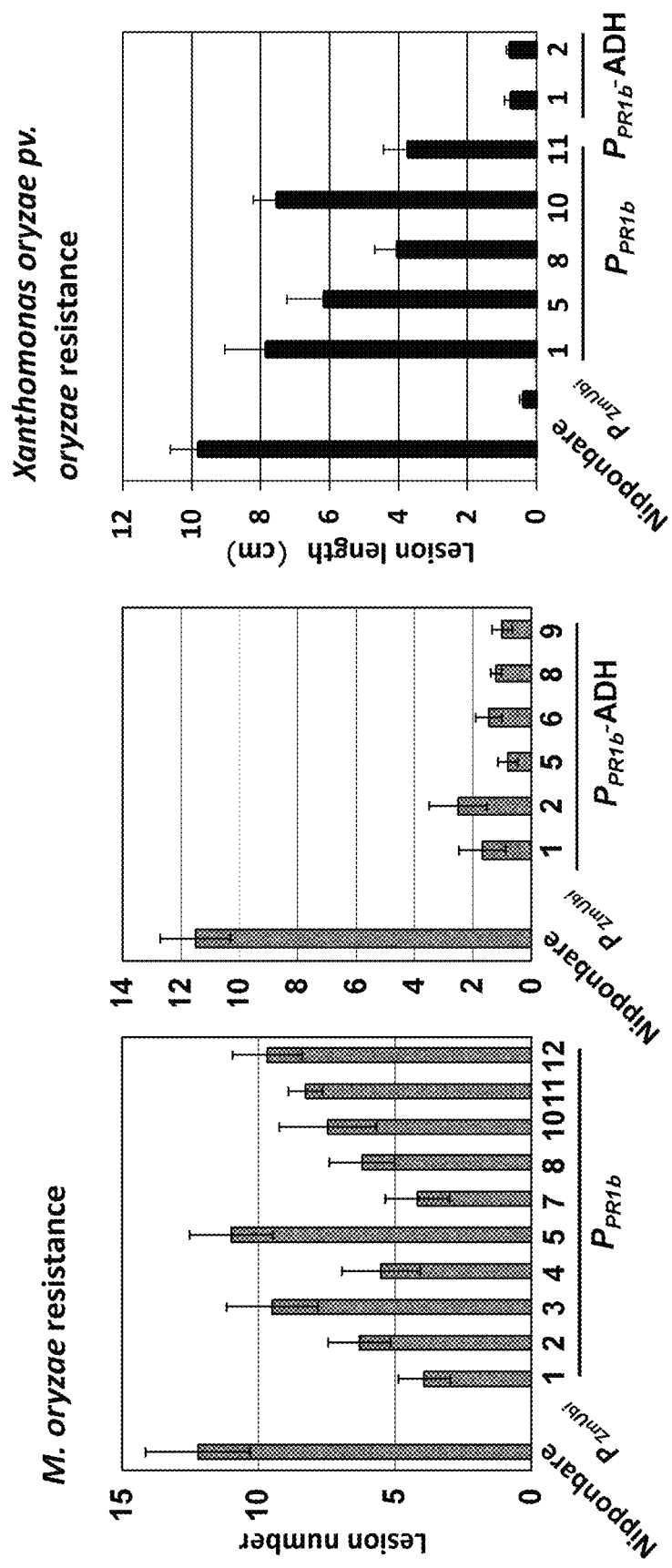
FIG. 3 shows disease resistance of the rice lines expressing OsWRKY45 by the $P_{PR1b}$ promoter. All lines used were homozygotes of the T2 generation. They were assayed for resistance to rice blast (*M. oryzae*) and bacterial leaf blight (Xoo) diseases.

The resistance of transformants to rice blast was tested as described in Example 2. As compared with those of non-transformants, in all of the Os WRKY45-expressing lines having any one of the nine promoters and no translational enhancer, the resistance to rice blast was almost unchanged, or a less-than-50% decrease in the number of lesions was seen (the $P_{GST}$ lines in FIG. 2 and $P_{PR1b}$ lines in FIG. 3). However, a very strong resistance was seen in the $P_{GST}$-ADH lines and $P_{PR1b}$-ADH lines with the translational enhancer (ADH-UTR) (the $P_{GST}$-ADH lines in FIG. 2 and $P_{PR1b}$-ADH lines in FIG. 3).

Example 8

Results of the Bacterial Leaf Blight Inoculation Test

The resistance of transformants to Xoo was tested as described in Example 3. As a result of the test, when the translational enhancer was not used, the resistance to bacterial leaf blight was almost unchanged or only an insufficient improvement was seen in all the Os WRKY45-expressing lines (the $P_{GST}$ lines in FIG. 2 and $P_{PR1b}$ lines in FIG. 3). However, a very strong resistance was seen in the $P_{GST}$-ADH lines and $P_{PR1b}$-ADH lines with the translational enhancer (ADH-UTR) (the $P_{GST}$-ADH lines in FIG. 2 and $P_{PR1b}$-ADH lines in FIG. 3).

Example 9

Results on the Growth and Yield of Os WRKY45-Expressing Lines Using the GST Promoter Lines expressing OsWRKY45 by $P_{GST}$ or $P_{GST}$-ADH were cultivated together with Nipponbare and the lines overexpressing OsWRKY45 by the Zmubi promoter in the isolation field that is not open to the public in Korea, and the growth and yield properties were examined. As a result, the plant height, fresh weight, fertility, and weight of 1,000 grains of the line with the Zmubi promoter were significantly impaired as compared to Nipponbare. The results for many of the $P_{GST}$ lines were nearly equivalent to those of Nipponbare. As for the $P_{GST}$-ADH lines, a significant improvement was seen for all traits as compared with lines carrying the Zmubi promoter. The plant height was overall shorter as compared with Nipponbare; however for the other traits, numerical values close to those of Nipponbare were obtained, and $P_{GST}$-ADH seems suitable for expressing OsWRKY45 (FIG. 4).

Example 10

Figure 5:
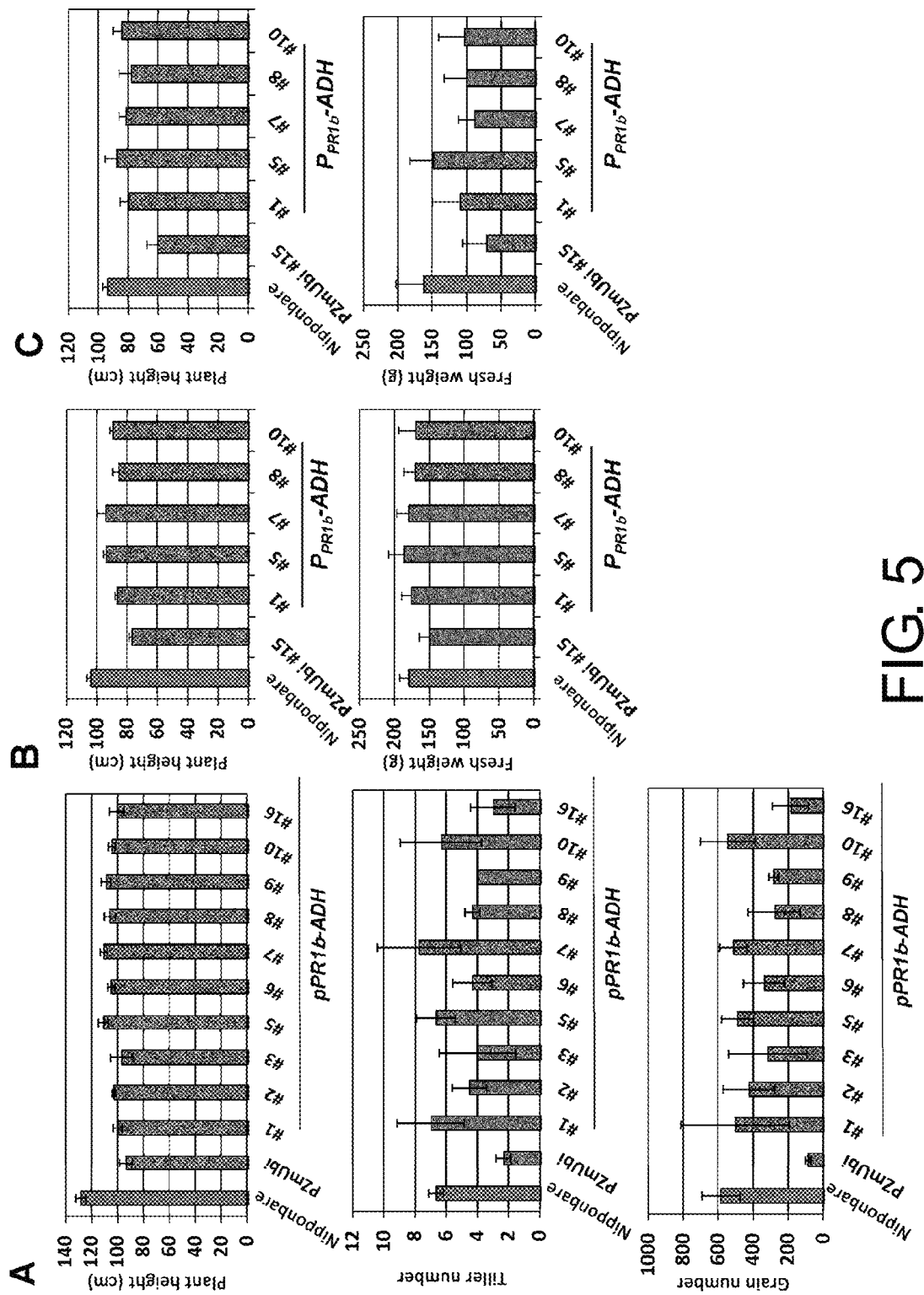
FIGS. 5A to 5C show the growth traits of the rice lines expressing WRKY45 by the PR1b promoter.

Results on the Growth and Yield of Os WRKY45-Expressing Lines Using the $P_{PR1b}$ Promoter The $P_{PR1b}$-ADH lines were cultivated under the following three conditions: program-regulated greenhouse (FIG. 5A), the external-environment-following greenhouse (FIG. 5B), or an isolation field in Korea (FIG. 5C). Then, the plant height, fresh weight, tiller number, grain number and such were measured. As a result, the $P_{PR1b}$-ADH lines showed more favorable numerical values in all evaluated items as compared with the lines overexpressing OsWRKY45 by the Zmubi promoter. Moreover, depending on the lines (in particular, #5), growth and yield nearly equivalent to those of Nipponbare were obtained.

From these results, it is believed that complex disease-resistant lines showing almost no adverse effect on agronomic traits could be generated by expressing OsWRKY45 using the PR1b promoter and a translation enhancer in combination.

Example 11

Results of Infection-Responsive OsWRKY45 Expression by the GST Promoter

Figure 6:
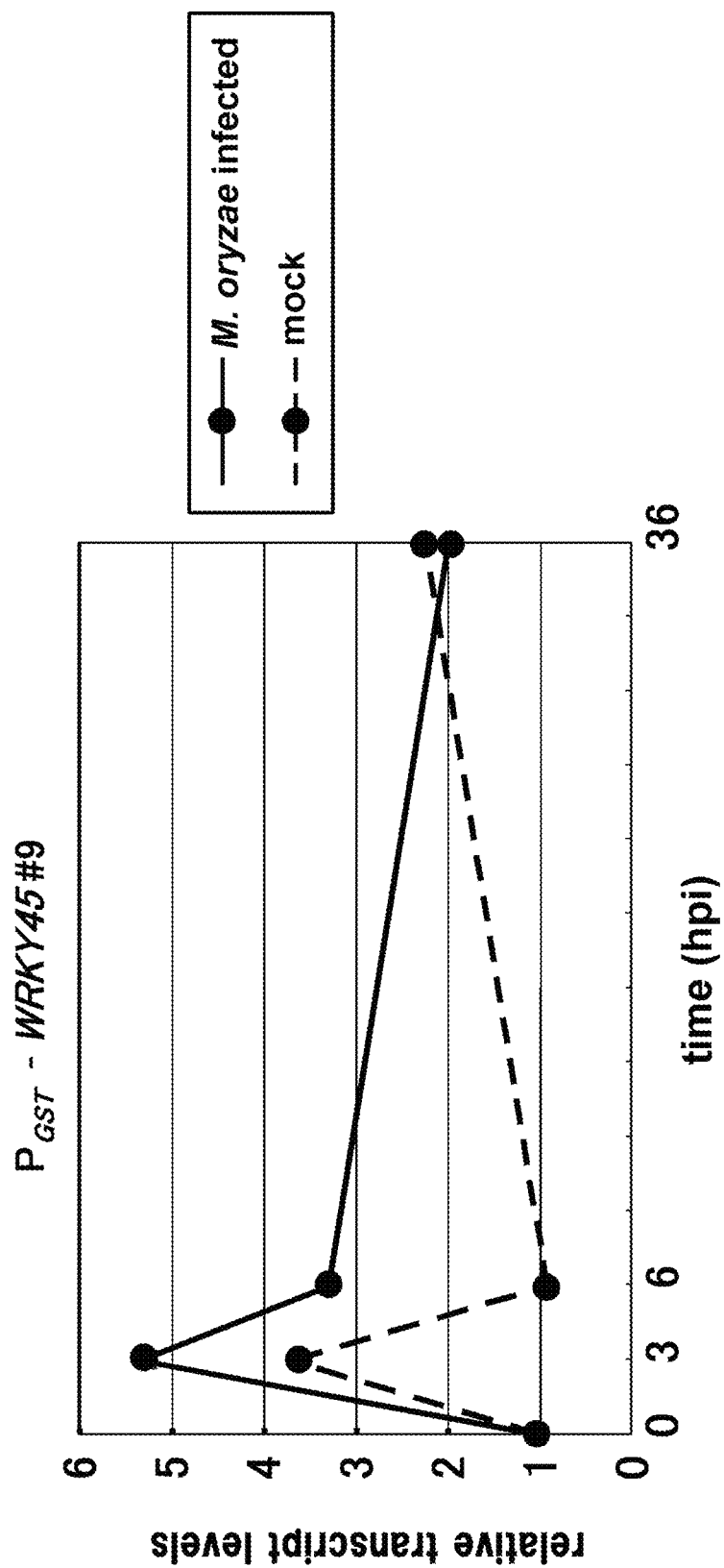
FIG. 6 shows the RNA expression pattern of the introduced OsWRKY45 transgene in a $P_{GST}$-OsWRKY45 line. Temporal patterns of the transcript levels of OsWRKY45 transgene after inoculation with compatible race of *M. oryzae* is shown as relative values over the expression levels before *M. oryzae* inoculation.

A line expressing OsWRKY45 by the GST promoter was inoculated with *M. oryzae*, and then OsWRKY45 transcripts derived from the introduced gene were examined. As a result, an increase in the transcript level was observed a few hours after inoculation (FIG. 6). From this result, it was confirmed that the GST promoter used activates at an early phase in response to infection by *M. oryzae*. Accordingly, use of a promoter activated at an early stage after infection by a pathogen may be important for providing plants with Os WRKY45-mediated disease resistance.

Example 12

Figure 7:
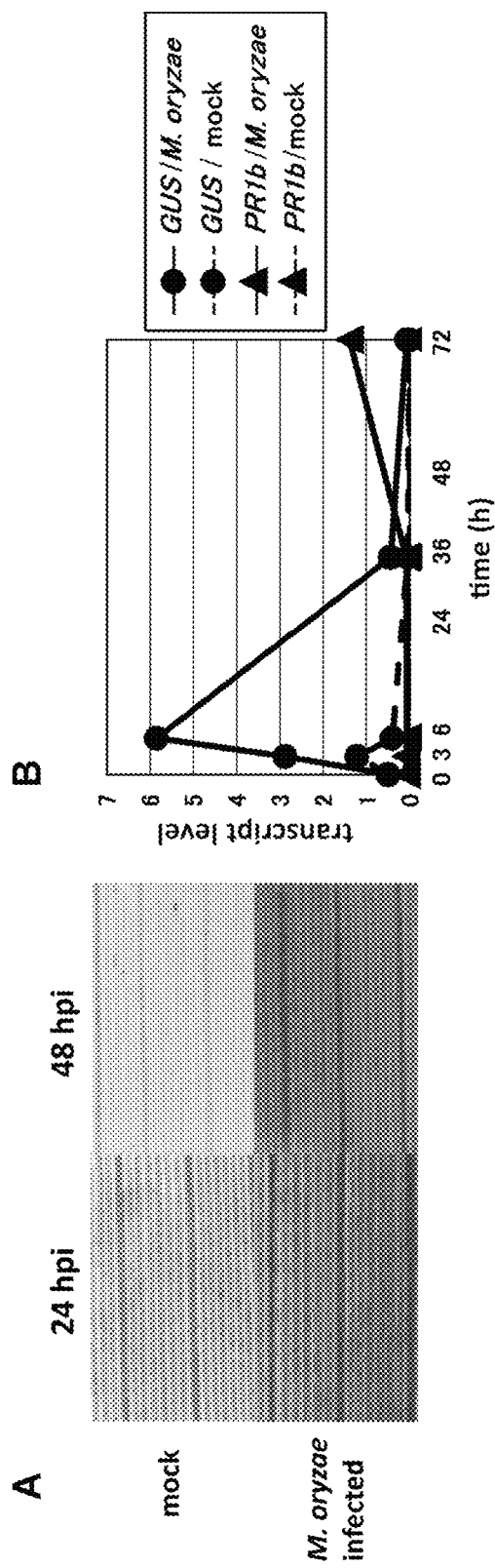
FIGS. 7A and 7B show the responsiveness of the PR1b promoter to *M. oryzae* infection.

Result of Analysis on the Infection Responsiveness of the PR1b Promoter Using the GUS Gene Transformed rice into which the PR1b promoter-GUS fusion gene was introduced was inoculated with compatible *M. oryzae* (race 007.0), and histochemical staining was carried out using X-Gluc as substrate. As a result, blue dye was observed throughout the inoculated leaves within 24 hours of inoculation. This indicates that the PR1b promoter was activated in response to the infection signal that spread throughout the infected leaves. Thus, by using this promoter to express OsWRKY45, the expression of OsWRKY45 may be induced in the entire infected leaves in response to *M. oryzae* infection (FIG. 7A). Examination of the transcript level revealed that the expression of GUS transcripts by the PR1b promoter was induced within a few hours of inoculation (FIG. 7B). Such early activation of the promoter after pathogen induction is important for driving the OsWRKY45 expression to prevent diseases. Induction of the endogenous PR1b gene expression occurred much later; therefore, it may be important to use only the 2 kb sequence upstream of the PR1b gene for early infection-responsive activation.

All publication and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in chemical engineering, cell biology, or molecular biology or related fields are intended to be within the scope of the following claims.

What is claimed is:

1. A transgenic plant comprising a WRKY45 gene, wherein the WRKY45 gene is operably linked to an infection-responsive promoter and a translational enhancer, wherein the infection-responsive promoter is the nucleotide sequence as set forth in SEQ ID NO: 3;
and wherein expression of said WRKY45 gene in the plant is induced in an infection-responsive manner.

2. The transgenic plant of claim 1, wherein the WRKY45 gene is a rice WRKY45 gene.

3. The transgenic plant of claim 2, wherein the WRKY45 gene has a nucleotide sequence encoding the amino acid sequence as set forth in SEQ ID NO: 2, or an amino acid sequence at least 95% identical to the sequence of SEQ ID NO: 2.

4. The transgenic plant of claim 1, wherein said expression of the WRKY45 gene is induced within six hours of infection.

5. The transgenic plant of claim 1, wherein the translational enhancer is an alcohol dehydrogenase 5'-untranslated region (ADH-UTR).

6. The transgenic plant of claim 5, wherein the alcohol dehydrogenase 5'-untranslated region (ADH-UTR) has the nucleotide sequence as set forth in SEQ ID NO: 5.

7. The transgenic plant of claim 1, wherein the WRKY45 gene is further operably linked to a tandem terminator comprising two terminator sequences in tandem.

8. The transgenic plant of claim 7, wherein the tandem terminator comprises a nopaline synthase (nos) terminator and Cauliflower mosaic virus 35S terminator.

9. The transgenic plant of claim 8, wherein the tandem terminator has the nucleotide sequence as set forth in SEQ ID NO: 6.

10. The transgenic plant of claim 1, wherein said expression of the WRKY45 gene is responsive to infection by a filamentous fungus.

11. The transgenic plant of claim 1, wherein said expression of the WRKY45 gene is responsive to infection by a bacterium.

12. The transgenic plant of claim 1, wherein the transgenic plant is a monocot.

13. The transgenic plant of claim 1, wherein the transgenic plant is rice.

14. A transgenic plant which is a progeny or clone of the transgenic plant of claim 1, wherein said progeny or clone comprises said WRKY45 gene operably linked to the infection-responsive promoter and the translational enhancer.

15. A propagation material of the transgenic plant of claim 1, wherein said propagation material comprises said WRKY45 gene operably linked to the infection-responsive promoter and the translational enhancer.

16. An isolated nucleic acid construct comprising a WRKY45 gene, wherein the WRKY45 gene is operably linked to an infection-responsive promoter and a translational enhancer, wherein the infection-responsive promoter is the nucleotide sequence as set forth in SEQ ID NO: 3.

17. A vector comprising the isolated nucleic acid construct of claim 16.

18. A plant cell into which the vector of claim 17 has been introduced.

19. A method for producing a transgenic plant, comprising the steps of:
   a) introducing the isolated nucleic acid construct of claim 16 into a plant cell; and
   b) regenerating a plant from the plant cell,
   wherein expression of said WRKY45 gene in the plant is induced in an infection-responsive manner.

20. A method for producing a plant which comprises a WRKY45 gene operably linked to an infection-responsive promoter and a translational enhancer, wherein the method comprises introducing the isolated nucleic acid construct of claim 16 into a plant.

21. An agent for producing a transgenic plant, wherein the agent comprises the isolated nucleic acid construct of claim 16.

* * * * *